US012758536B2

(12) United States Patent
Smith et al.

(10) Patent No.: US 12,758,536 B2
(45) Date of Patent: Oct. 13, 2026

(54) COMBINATION OF A SK2 INHIBITOR AND AN INHIBITOR OF A CHECKPOINT PATHWAY, USES AND PHARMACEUTICAL COMPOSITIONS THEREOF

(71) Applicant: Apogee Biotechnology Corporation, Hummelstown, PA (US)

(72) Inventors: Charles D. Smith, Hummelstown, PA (US); Lynn W. Maines, Hummelstown, PA (US)

(73) Assignee: Apogee Biotechnology Corporation, Hummelstown, PA (US)

( * ) Notice: Subject to any disclaimer, the term of this patent is extended or adjusted under 35 U.S.C. 154(b) by 888 days.

(21) Appl. No.: 17/422,647

(22) PCT Filed: Jan. 16, 2020

(86) PCT No.: PCT/US2020/013817

§ 371 (c)(1),
(2) Date: Jul. 13, 2021

(87) PCT Pub. No.: WO2020/150434

PCT Pub. Date: Jul. 23, 2020

(65) Prior Publication Data

US 2022/0062250 A1 Mar. 3, 2022

Related U.S. Application Data

(60) Provisional application No. 62/792,996, filed on Jan. 16, 2019.

(51) Int. Cl.

| | |
|---|---|
| *A61K 31/4409* | (2006.01) |
| *A61P 35/00* | (2006.01) |
| *C07K 16/28* | (2006.01) |

(52) U.S. Cl.
CPC .......... *A61K 31/4409* (2013.01); *A61P 35/00* (2018.01); *C07K 16/2818* (2013.01); *C07K 16/2827* (2013.01)

(58) Field of Classification Search
None
See application file for complete search history.

(56) References Cited

U.S. PATENT DOCUMENTS 8,063,248 B2 11/2011 Smith et al.
8,263,344 B2 9/2012 Kroemer et al.
(Continued)

FOREIGN PATENT DOCUMENTS

CN 101248041 A 8/2008
JP 2018-533560 A 11/2018
(Continued)

OTHER PUBLICATIONS

Domagala et al., Int J Mol Sci. Aug. 1, 2018;19(8):2256 (Year: 2018).*

(Continued)

*Primary Examiner* — Jeffrey S Lundgren
*Assistant Examiner* — Anthony Joseph Seitz
(74) *Attorney, Agent, or Firm* — GREENBERG TRAURIG, LLP

(57) ABSTRACT

A method or preparing immunologically primed cancer cells using cancer cells collected from a patient includes treating the collected cancer cells, ex vivo, with a toxic concentration of a compound that modifies sphingolipid metabolism, wherein the toxic concentration is sufficient to induce immunogenic cell death in the cancer cells. In an embodiment, the compound is 3-(4-Chloro-phenyl)-adamantane-1-carboxylic acid(pyridin-4-ylmethyl)-amide compound or a pharmaceutically acceptable salt thereof. In an embodiment, the immunologically primed cancer cells overexpress calreticulin on (Continued)

their surface. In an embodiment, the cancer cells are solid tumor cells. In an embodiment, the cancer cells are circulating tumor cells. In an embodiment, the method further comprises harvesting at least a portion of the immunologically primed cancer cells; and suspending the cells in phosphate-buffered saline. In an embodiment, the method further comprises shipping at least a portion of the immunologically primed cancer cells to a point of the patient's care.

5 Claims, 9 Drawing Sheets

(56) References Cited

U.S. PATENT DOCUMENTS

| | | | | |
|---|---|---|---|---|
| 9,844,540 | B2 | 12/2017 | Fathi et al. | |
| 2010/0015653 | A1 | 1/2010 | Kroemer et al. | |
| 2012/0035268 | A1 * | 2/2012 | Szulc | A61P 9/00 564/240 |
| 2018/0369212 | A1 | 12/2018 | Rabbani et al. | |

FOREIGN PATENT DOCUMENTS

| | | | | | |
|---|---|---|---|---|---|
| RU | 2447060 | C2 | | 4/2012 | |
| WO | 2016063134 | A1 | | 4/2016 | |
| WO | WO-2017060771 | A2 | * | 4/2017 | A61P 35/00 |
| WO | WO-2017129769 | A1 | * | 8/2017 | A61K 31/426 |
| WO | 2020208060 | A1 | | 10/2020 | |

OTHER PUBLICATIONS

Maceyka et al., The Journal of Biological Chemistry vol. 280, No. 44, p. 37118-37129, Nov. 4, 2005 (Year: 2005).*

International Search Report and Written Opinion from International Application No. PCT/US2020/013817 dated Apr. 24, 2020.

Lewis C. S., Voelkel-Johnson C., Smith C. D. Targeting sphingosine kinases for the treatment of cancer // Advances in cancer research.—2018—140.—p. 295-325.

Beljanski V., Knaak C., Smith C. D. A novel sphingosine kinase inhibitor induces autophagy in tumor cells // Journal of Pharmacology and Experimental Therapeutics.—2010—333(2)—p. 454-464.

Llovet Josep M et al: "Molecular therapies and precision medicine for hepatocellular carcinoma", Nature Reviews Clinical Oncology, Nature, NY, US, vol. 15, No. 10, Jul. 30, 2018 (Jul. 30, 2018), pp. 599-616, XP036596488, ISSN: 1759-4774, DOI: 10.1038/S41571-018-0073-4 [retrieved on Jul. 30, 2018].

Lu Dai et al: "The sphingosine kinase 2 inhibitor ABC294640 displays anti-non-small cell lung cancer activities in vitro and in viva", International Journal of Cancer, John Wiley & Sons, Inc, US, vol. 142, No. 10, Jan. 4, 2018 (Jan. 4, 2018), pp. 2153-2162, XP071290130, ISSN: 0020-7136, DOI: 10.1002/IJC.31234.

H. Venant et al: "The Sphingosine Kinase 2 Inhibitor ABC294640 Reduces the Growth of Prostate Cancer Cells and Results in Accumulation of Dihydroceramides In Vitro and In Vivo", Molecular Cancer Therapeutics, vol. 14, No. 12, Dec. 1, 2015 (Dec. 1, 2015), pp. 2744-2752, XP055705150, US ISSN: 1535-7163, DOI: 10.1158/1535-7163.MCT-15-0279.

Peng Gao, Yuri K. Peterson, Ryan A. Smith, Charles D. Smith: Characterization of Isoenzyme-Selective Inhibitors of Human Sphingosine Kinases, Journal, Sep. 2012, pp. 1-11 , vol. 7, Issue 9.

Kevin J. French, et al.: Pharmacology and Antitumor Activity of ABC294640, a Selective Inhibitor of Sphingosine Kinase-2, Journal, Jan. 7, 2010, pp. 129-139, vol. 333.

Maceyka et al., "SphK1 and SphK2, Sphingosine Kinase Isoenzymes with Opposing Functions in Sphingolipid Metabolism," The Journal of Biological Chemistry, vol. 280, No. 44, pp. 37118-37129, Nov. 4, 2005.

Liu et al., "Sphingosine Kinase Type 2 Is a Putative BH3-only Protein That Induces Apoptosis," The Journal of Biological Chemistry, vol. 278, No. 41, Issue of Oct. 10, pp. 40330-40336, 2003.

* cited by examiner

COMBINATION OF A SK2 INHIBITOR AND AN INHIBITOR OF A CHECKPOINT PATHWAY, USES AND PHARMACEUTICAL COMPOSITIONS THEREOF

CROSS REFERENCE TO RELATED APPLICATIONS

This application is a U.S. national phase application under 35 U.S.C. 371 of PCT International Application No. PCT/US2020/013817, filed Jan. 16, 2020, which claims priority to and the benefit of U.S. Provisional Application Ser. No. 62/792,996, filed Jan. 16, 2019, the entire contents of each of which are hereby incorporated by reference in their entireties.

BACKGROUND

Cancer is a group of diseases characterized by the uncontrolled growth and spread of abnormal cells. There are many different types of cancer treatment, including traditional therapies (such as surgery, chemotherapy, and radiation therapy), newer forms of treatment (targeted therapy), and complementary and alternative therapies. It is becoming increasingly evident that cancers are dependent on a number of altered molecular pathways and can develop diverse mechanisms of resistance to therapy with single agents. Therefore, combination regimens may provide the best hope for effective therapies with durable effects.

SUMMARY

According to aspects illustrated herein, there is disclosed an immunogenic cell death (ICD) inducer comprising a toxic concentration of a selective inhibitor of sphingosine kinase-2 (SK2). In an embodiment, the selective inhibitor of SK2 is 3-(4-Chloro-phenyl)-adamantane-1-carboxylic acid (pyridin-4-ylmethyl)-amide compound or a pharmaceutically acceptable salt thereof. In an embodiment, the toxic concentration of 3-(4-Chloro-phenyl)-adamantane-1-carboxylic acid (pyridin-4-ylmethyl)-amide compound or a pharmaceutically acceptable salt thereof is from about 35 μM to about 45 M. In an embodiment, cancer cells from a patient are treated in vitro with about 35 μM to about 45 μM of 3-(4-Chloro-phenyl)-adamantane-1-carboxylic acid (pyridin-4-ylmethyl)-amide compound or a pharmaceutically acceptable salt thereof so as to result in sufficient immunogenic cell death (ICD) in the cancer cells. These primed cancer cells can be used as cancer immunotherapy and administered back to the patient. In an embodiment, these newly implanted primed cancer cells can evoke large-scale ICD in untreated cancer cells within the patient.

According to aspects illustrated herein, there is disclosed a method of preparing immunologically primed cancer cells using cancer cells collected from a patient that includes treating the cancer cells, ex vivo, with a toxic concentration of a compound that modifies sphingolipid metabolism, wherein the toxic concentration is sufficient to induce immunogenic cell death in the cancer cells. In an embodiment, the compound that modifies sphingolipid metabolism is an inhibitor of a sphingosine kinase. In an embodiment, the compound that is an inhibitor of a sphingosine kinase is a selective inhibitor of sphingosine kinase-2 (SK2). In an embodiment, the selective inhibitor of SK2 is 3-(4-Chloro-phenyl)-adamantane-1-carboxylic acid (pyridin-4-ylmethyl)-amide compound or a pharmaceutically acceptable salt thereof. In an embodiment, the collected cancer cells are treated for at least 24 hours. In an embodiment, the toxic concentration of the selective inhibitor of SK2 is from about 20 M to about 60 μM. In an embodiment, the immunologically primed cancer cells overexpress calreticulin on their surface. In an embodiment, the cancer cells are immune cells. In an embodiment, the immune cells comprise T-cells, natural killer (NK) cells, or dendritic cells. In an embodiment, the cancer cells are hematologic cancer cells. In an embodiment, the hematologic cancer cells are leukemia cells. In an embodiment, the cancer cells are solid tumor cells. In an embodiment, the cancer cells are circulating tumor cells. In an embodiment, the method further comprises harvesting at least a portion of the immunologically primed cancer cells and suspending the cells in phosphate-buffered saline. In an embodiment, the method further comprises shipping at least a portion of the immunologically primed cancer cells to a point of the patient's care. In an embodiment, the point of the patient's care is a hospital. In an embodiment, the point of the patient's care is a cancer center. In an embodiment, the method further comprises administering at least a portion of the shipped immunologically primed cancer cells to the patient to elicit an immune response. In an embodiment, the immune response slows or stops the growth of cancer in the patient. In an embodiment, the immune response stops cancer from metastasizing in the patient. In an embodiment, the immune response makes the patients immune system more efficient at killing cancer cells. In an embodiment, the method further comprises administering an effective amount of at least one checkpoint inhibitor.

According to aspects illustrated herein, there is disclosed a method of inducing an anti-cancer immune response in a patient, comprising removing cancer cells from the patient and treating the cells ex vivo with 3-(4-Chloro-phenyl)-adamantane-1-carboxylic acid (pyridin-4-ylmethyl)-amide compound of a pharmaceutically acceptable salt thereof incorporated in a pharmaceutically acceptable formulation in amounts sufficient to induce, enhance, or promote immunogenic cell death in the cancer cells, and then administration of the treated cells back to the original patient to elicit an immune response against the patient's cancer. In an embodiment, the cells of the patient are hematologic cancer cells, such as leukemia cells. In an embodiment, the cells of the patient are solid tumor cells obtained by biopsy or circulating tumor cells isolated from the patient's blood.

According to aspects illustrated herein, there is disclosed an effective amount of an inhibitor of sphingosine kinase and an effective amount of at least one checkpoint inhibitor selected from the group consisting of a CTLA-4 receptor inhibitor, PD-1 receptor inhibitor, PD-L1 ligand inhibitor, PD-L2 ligand inhibitor, a LAG-3 receptor inhibitor, a TIM-3 receptor inhibitor, a BTLA receptor inhibitor, a KIR receptor inhibitor, or a combination of any of the foregoing checkpoint inhibitors, for use in a method of treating a cancer in a subject. In an embodiment, the checkpoint inhibitor is an inhibitor of the PD-L1/PD-1 pathway. In an embodiment, the checkpoint inhibitor is an inhibitor of CTLA-4. In an embodiment, the cancer is a chemotherapy or radio-resistant cancer. In an embodiment, the inhibitor of sphingosine kinase is administered and then the other inhibitor is administered within a suitable period of time. In an embodiment, the inhibitor of sphingosine kinase is an inhibitor of sphingosine-kinase-2. In an embodiment, the inhibitor of sphingosine-kinase-2 is 3-(4-Chloro-phenyl)-adamantane-1-carboxylic acid (pyridin-4-ylmethyl)-amide (ABC294640). In an embodiment, the inhibitor of the PD-L1/PD-1 pathway is an anti-PD-L1 antibody, an anti-PD-1 antibody or combinations thereof. In an embodiment, the anti-PD-L1 antibody or an anti-PD-1 antibody is a monoclonal antibody. In an embodiment, the monoclonal antibody is a human antibody or a humanized antibody. In an embodiment, the inhibitor of CTLA-4 is an anti-CTLA-4 antibody. In an embodiment, the anti-CTLA-4 antibody is a monoclonal antibody. In an embodiment, the monoclonal antibody is a human antibody or a humanized antibody.

According to aspects illustrated herein, there is disclosed a method of treating cancer in a subject comprising administering to the subject an effective amount of an inhibitor of sphingosine kinase (SK) and an effective amount of a checkpoint inhibitor. In an embodiment, the checkpoint inhibitor can be an antibody directed toward CTLA4 (for example Ipilimumab) or directed toward PD-1 (for example Pembrolizumab or Nivolumab) or directed toward PD-L1 (for example Atezolizumab or Durvalumab). Other antibodies or chemical inhibitors targeting these pathways are also within the scope of this invention. For example, additional inhibitors of the PD-L1 pathway include BMS-936559, MPDL3280A, BMS-936558, MK-3475, CT-011, or MEDI4736.

According to aspects illustrated herein, there is disclosed a method of treating a cancer in a patient comprising administering to the patient an effective amount of an inhibitor of sphingosine kinase and at least one of the following: an inhibitor of the PD-L1/PD-1 pathway or an inhibitor of CTLA-4. In an embodiment, the inhibitor of sphingosine kinase is an inhibitor of sphingosine-kinase-2. In an embodiment, the inhibitor of sphingosine-kinase-2 is 3-(4-Chloro-phenyl)-adamantane-1-carboxylic acid (pyridin-4-ylmethyl)-amide (ABC294640). In an embodiment, the inhibitor of the PD-L1/PD-1 pathway is an anti-PD-L1 antibody, an anti-PD-1 antibody or combinations thereof. In an embodiment, the anti-PD-L1 antibody or an anti-PD-1 antibody is a monoclonal antibody. In an embodiment, the monoclonal antibody is a human antibody or a humanized antibody. In an embodiment, the inhibitor of CTLA-4 is an anti-CTLA-4 antibody. In an embodiment, the anti-CTLA-4 antibody is a monoclonal antibody. In an embodiment, the monoclonal antibody is a human antibody or a humanized antibody.

According to aspects illustrated herein, there is disclosed a method of treating melanoma in a patient in need thereof comprising administering to the patient an effective amount of an inhibitor of sphingosine kinase and an inhibitor of CTLA-4. In an embodiment, the inhibitor of sphingosine kinase is an inhibitor of sphingosine-kinase-2. In an embodiment, the inhibitor of sphingosine-kinase-2 is 3-(4-Chloro-phenyl)-adamantane-1-carboxylic acid (pyridin-4-ylmethyl)-amide (ABC294640). In an embodiment, the inhibitor of CTLA-4 is an anti-CTLA-4 antibody. In an embodiment, the anti-CTLA-4 antibody is a monoclonal antibody. In an embodiment, the monoclonal antibody is a human antibody or a humanized antibody. In an embodiment, the treating melanoma is further defined as reducing the size of a tumor or inhibiting growth of a tumor. In an embodiment, the inhibitors are administered to the patient in need thereof at least two, three, four, five, six, seven, eight, nine or ten times. In an embodiment, the patient is further administered a second cancer therapy. In an embodiment, the second cancer therapy comprises surgery, radiotherapy, chemotherapy, toxin therapy, immunotherapy, cryotherapy or gene therapy. In an embodiment, the melanoma is a chemotherapy or radio-resistant melanoma.

According to aspects illustrated herein, there is disclosed a method of treating melanoma in a patient in need thereof comprising administering to the patient an effective amount of an inhibitor of sphingosine kinase and an inhibitor of the PD-L1/PD-1 pathway. In an embodiment, the inhibitor of sphingosine kinase is an inhibitor of sphingosine-kinase-2. In an embodiment, the inhibitor of sphingosine-kinase-2 is 3-(4-Chloro-phenyl)-adamantane-1-carboxylic acid (pyridin-4-ylmethyl)-amide (ABC294640). In an embodiment, the inhibitor of the PD-L1/PD-1 pathway is an anti-PD-L1 antibody, an anti-PD-1 antibody or combinations thereof. In an embodiment, the anti-PD-L1 antibody or an anti-PD-1 antibody is a monoclonal antibody. In an embodiment, the monoclonal antibody is a human antibody or a humanized antibody. In an embodiment, the treating melanoma is further defined as reducing the size of a tumor or inhibiting growth of a tumor. In an embodiment, the inhibitors are administered to the patient at least two, three, four, five, six, seven, eight, nine or ten times. In an embodiment, the patient is further administered a second cancer therapy. In an embodiment, the second cancer therapy comprises surgery, radiotherapy, chemotherapy, toxin therapy, immunotherapy, cryotherapy or gene therapy. In an embodiment, the melanoma is a chemotherapy or radio-resistant melanoma.

According to aspects illustrated herein, there is disclosed a method of treating melanoma in a patient in need thereof comprising administering to the patient an effective amount of 3-(4-Chloro-phenyl)-adamantane-1-carboxylic acid (pyridin-4-ylmethyl)-amide (ABC294640) and an inhibitor of the PD-L1 pathway.

According to aspects illustrated herein, there is disclosed a method of treating a patient afflicted with a lung cancer comprising administering to the patient in need thereof a therapeutically effective amount of an anti-cancer agent which is an antibody or an antigen-binding portion thereof that binds specifically to a PD-1 receptor and inhibits PD-1 activity ("an anti-PD-1 antibody or antigen-binding portion thereof"), which is administered by infusion for less than 60 minutes, in combination with an inhibitor of sphingosine kinase which is administered orally. In an embodiment, the inhibitor of sphingosine kinase is an inhibitor of sphingosine-kinase-2. In an embodiment, the inhibitor of sphingosine-kinase-2 is 3-(4-Chloro-phenyl)-adamantane-1-carboxylic acid (pyridin-4-ylmethyl)-amide (ABC294640).

According to aspects illustrated herein, there is disclosed a method for treating a patient afflicted with a lung cancer comprising administering to the patient in need thereof a flat dose of a therapeutically effective amount of an anti-cancer agent which is an antibody or an antigen-binding portion thereof that binds specifically to PD-1 receptor and inhibits PD-1 activity in combination with a therapeutically effective amount of an inhibitor of sphingosine kinase which is administered orally. In an embodiment, the inhibitor of sphingosine kinase is an inhibitor of sphingosine-kinase-2. In an embodiment, the inhibitor of sphingosine-kinase-2 is 3-(4-Chloro-phenyl)-adamantane-1-carboxylic acid (pyridin-4-ylmethyl)-amide (ABC294640).

According to aspects illustrated herein, there is disclosed a method of treating lung cancer in a patient comprising administering to the patient in need thereof an effective amount of an inhibitor of sphingosine kinase and an inhibitor of anti-CTLA-4. In an embodiment, the inhibitor of sphingosine kinase is an inhibitor of sphingosine-kinase-2. In an embodiment, the inhibitor of sphingosine-kinase-2 is 3-(4-Chloro-phenyl)-adamantane-1-carboxylic acid (pyridin-4-ylmethyl)-amide (ABC294640). In an embodiment, the inhibitor of anti-CTLA-4 is an anti-CTLA-4 antibody. In an embodiment, the anti-CTLA-4 antibody is a monoclonal antibody. In an embodiment, the monoclonal antibody is a human antibody or a humanized antibody. In an embodiment, the anti-CTLA-4 monoclonal antibody is ipilimumab. In an embodiment, the treating lung cancer is further defined as reducing the size of a tumor or inhibiting growth of a tumor. In an embodiment, the inhibitors are administered to the patient at least two, three, four, five, six, seven, eight, nine or ten times. In an embodiment, the patient is further administered a second cancer therapy. In an embodiment, the second cancer therapy comprises surgery, radiotherapy, chemotherapy, toxin therapy, immunotherapy, cryotherapy or gene therapy.

According to aspects illustrated herein, there is disclosed a method of treating lung cancer in a patient in need thereof comprising administering to the patient an effective amount of 3-(4-Chloro-phenyl)-adamantane-1-carboxylic acid (pyridin-4-ylmethyl)-amide (ABC294640) and an inhibitor of anti-CTLA-4. In an embodiment, the inhibitor of anti-CTLA-4 is an anti-CTLA-4 antibody. In an embodiment, the anti-CTLA-4 antibody is a monoclonal antibody. In an embodiment, the anti-CTLA-4 monoclonal antibody is ipilimumab.

According to aspects illustrated herein, there is disclosed a kit for preparing cells for immunogenic cell death. The kit comprises a toxic concentration of a compound that modifies sphingolipid metabolism, wherein the toxic concentration is sufficient to induce immunogenic cell death in the cancer cells; and a set of instructions for use. In an embodiment, the compound that modifies sphingolipid metabolism is an inhibitor of a sphingosine kinase. In an embodiment, the compound that is an inhibitor of a sphingosine kinase is a selective inhibitor of sphingosine kinase-2 (SK2). In an embodiment, the selective inhibitor of SK2 is 3-(4-Chloro-phenyl)-adamantane-1-carboxylic acid (pyridin-4-ylmethyl)-amide compound or a pharmaceutically acceptable salt thereof. In an embodiment, the toxic concentration of the selective inhibitor of SK2 is from about 20 μM to about 60 μM.

According to aspects illustrated herein, there is disclosed a kit for treating a tumor. The kit can comprise at least one checkpoint inhibitor compound; 3-(4-Chloro-phenyl)-adamantane-1-carboxylic acid (pyridin-4-ylmethyl)-amide, or a pharmaceutically acceptable salt thereof; and a set of instructions for use. In an embodiment, the instructions for use include a label indicating how to administer the inhibitors, including route of administration, dose of administration and a time period for administration. In some embodiments of the kit, the 3-(4-Chloro-phenyl)-adamantane-1-carboxylic acid (pyridin-4-ylmethyl)-amide, or a pharmaceutically acceptable salt thereof is stored in a separate container from the at least one immune checkpoint inhibitor compound. In some embodiments of the kit, the at least one immune checkpoint inhibitor compound is a CTLA-4 receptor inhibitor, PD-1 receptor inhibitor, PD-L1 inhibitor, or PD-L2 inhibitor, a LAG-3 receptor inhibitor, a TIM-3 receptor inhibitor, a BTLA receptor inhibitor, a KIR receptor inhibitor, or a combination of any of the foregoing immune checkpoint inhibitor compounds. In some embodiments of the kit, the immune checkpoint inhibitor compound is an antibody or an antibody fragment. In some embodiments of the kit, the at least one immune checkpoint inhibitor compound is an anti-CTLA-4 receptor antibody, an anti-PD-1 receptor antibody, an anti-LAG-3 receptor antibody, an anti-TIM-3 receptor antibody, an anti-BTLA receptor antibody, an anti-KIR receptor antibody, an anti-PD-L1 antibody, or an anti-PD-L2 antibody, or a combination of any of the foregoing antibodies. In some embodiments of the kit, the at least one immune checkpoint inhibitor compound is in the form of a lyophilized solid. In some embodiments, the kit, further comprises an aqueous reconstitution solvent. In some embodiments of the kit, the at least one immune checkpoint inhibitor compound is incorporated in a first pharmaceutically acceptable formulation and the 3-(4-Chloro-phenyl)-adamantane-1-carboxylic acid (pyridin-4-ylmethyl)-amide is incorporated in a second pharmaceutically acceptable formulation.

According to aspects illustrated herein, there is disclosed a kit for treating a subject afflicted with a lung cancer, the kit comprising: a flat dosage of at least about 240 mg of an antibody or an antigen-binding portion thereof that specifically binds to the PD-1 receptor and inhibits PD-1 activity; a dosage of an inhibitor of sphingosine kinase; and instructions for using the anti-PD-1 antibody or antigen-binding portion thereof and the inhibitor of sphingosine kinase in a method of the present disclosure. In an embodiment, the instructions for use include a label indicating how to administer the anti-PD-1 antibody or antigen-binding portion thereof and the inhibitor of sphingosine kinase, including route of administration, dose of administration and a time period for administration. In an embodiment, the kit further includes a dosage of another anti-cancer agent which is a dosage ranging from 0.1 to 10 mg/kg body weight of an antibody or an antigen-binding portion thereof that specifically binds to and inhibits CTLA-4 and the instructions further described how to use the anti-CTLA-4 antibody or antigen-binding fragment thereof.

According to aspects illustrated herein, there is disclosed a kit for treating a subject afflicted with a lung cancer, the kit comprising: a dosage ranging from 0.1 to 10 mg/kg body weight of an anti-cancer agent which is an antibody or an antigen-binding portion thereof that specifically binds to the PD-1 receptor and inhibits PD-1 activity; a dosage of an inhibitor of sphingosine kinase; and instructions for using the anti-PD-1 antibody or antigen-binding portion thereof and the inhibitor of sphingosine kinase in a method of the present disclosure. In an embodiment, the kit further includes a dosage of another anti-cancer agent which is a dosage ranging from 0.1 to 10 mg/kg body weight of an antibody or an antigen-binding portion thereof that specifically binds to and inhibits CTLA-4 and the instructions further described how to use the anti-CTLA-4 antibody or antigen-binding fragment thereof.

According to aspects of the present disclosure, the cancer to be treated is selected from the group consisting of melanoma, cutaneous T-cell lymphoma, non-Hodgkin lymphoma, Mycosis fungoides, Pagetoid reticulosis, Sezary syndrome, Granulomatous slack skin, Lymphomatoid papulosis, *Pityriasis lichenoides* chronica, *Pityriasis lichenoides* et varioliformis *acuta*, CD30+ cutaneous T-cell lymphoma, Secondary cutaneous CD30+ large cell lymphoma, non-mycosis fungoides CD30 cutaneous large T-cell lymphoma, Pleomorphic T-cell lymphoma, Lennert lymphoma, subcutaneous T-cell lymphoma, angiocentric lymphoma, blastic NK-cell lymphoma, B-cell Lymphomas, hodgkins Lymphoma (HL), Head and neck tumor; Squamous cell carcinoma, rhabdomyocarcoma, non-small cell lung cancer, small cell lung cancer, esophageal squamous cell carcinoma, esophageal adenocarcinoma, renal cell carcinoma (RCC), colorectal cancer (CRC), acute myeloid leukemia (AML), breast cancer, cervical cancer, ovarian cancer, prostate cancer, testicular cancer, urothelial carcinoma, bladder cancer, gastric cancer, prostatic small cell neuroendocrine carcinoma (SCNC), liver cancer, sarcoma, glioblastoma, liver cancer, oral squamous cell carcinoma, pancreatic cancer, kidney cancer, thyroid papillary cancer, intrahepatic cholangiocellular carcinoma, hepatocellular carcinoma, bone cancer, metastasis, and nasopharyngeal carcinoma. In an embodiment, the treating cancer is further defined as reducing the size of a tumor or inhibiting growth of a tumor.

According to aspects of the present disclosure, the inhibitors may be administered to the subject in need thereof at least two, three, four, five, six, seven, eight, nine or ten times. In an embodiment of the present disclosure, the subject in need thereof is further administered a second cancer therapy. In an embodiment, the second cancer therapy comprises surgery, radiotherapy, chemotherapy, toxin therapy, immunotherapy, cryotherapy or gene therapy. In an embodiment, the cancer is a chemotherapy or radioresistant cancer.

DETAILED DESCRIPTION

Figure 1:
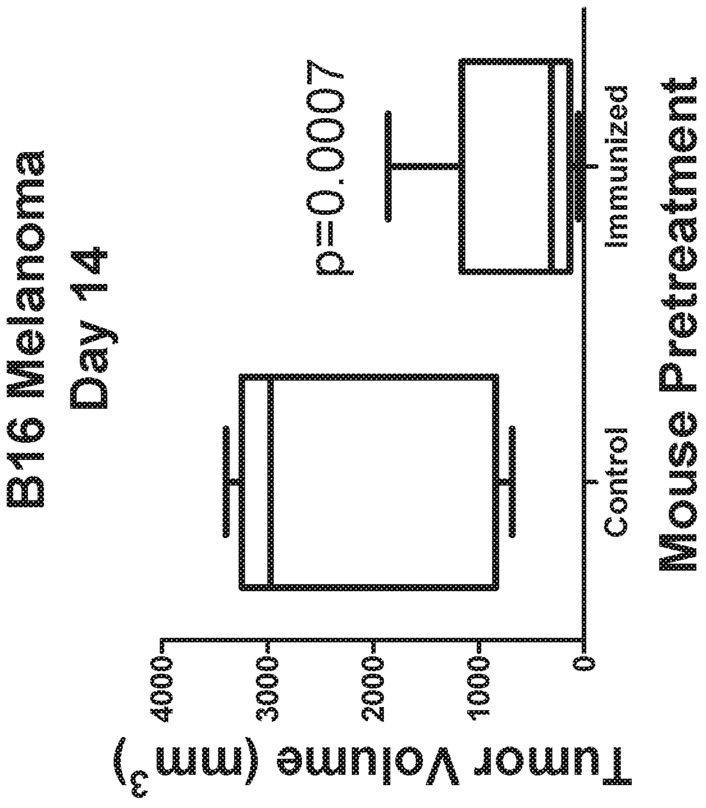
FIG. 1 shows that administration of ABC294640-treated B16 melanoma cells elicits immunity against subsequently injected untreated B16 tumor cells. This is demonstration that ABC294640 induces immunogenic cell death in tumor cells. For the "box & whiskers" plots shown in FIGS. 1, 2 and 3A-3C, the median tumor volume is indicated by the horizontal line in each bar; the range of the bar indicates the interquartile range; and the whiskers indicate the range between the smallest and largest tumors for each treatment group.

A sphingosine kinase (SK) inhibitor of the present disclosure is to be used in combination with one or more other anti-cancer therapies. Such other drugs may be administered, by a route and in an amount commonly used therefor, contemporaneously or sequentially with a SK inhibitor of the present invention. When a SK inhibitor of the present invention is used contemporaneously with one or more other drugs, a pharmaceutical composition containing such other drugs in addition to a SK inhibitor of the present invention is preferred. Accordingly, the pharmaceutical compositions of the present invention include those that also contain one or more other active ingredients or therapeutic agents, in addition to a SK inhibitor of the present invention. Examples of other therapeutic agents that may be combined with a SK inhibitor of the present invention, either administered separately or in the same pharmaceutical compositions, include, but are not limited to, an antibody against CTLA-4, PD1, or PD-L1. The weight ratio of the SK inhibitor of the present invention to the second active ingredient may be varied and will depend upon the effective dose of each ingredient. Generally, an effective dose of each will be used. Combinations of a SK inhibitor of the present invention and other active ingredients will generally also be within the aforementioned range, but in each case, an effective dose of each active ingredient should be used. In an embodiment, the SK inhibitor is used in combination with a checkpoint inhibitor. In an embodiment, the SK inhibitor is used in combination with one or more of a compound that blocks the activity of CTLA-4 (CD152), PD-1 (CD279), PDL-1 (CD274), TIM-3, LAG-3 (CD223), VISTA, KIR, NKG2A, BTLA, PD-1H, TIGIT, CD96, 4-1BB (CD137), 4-1BBL (CD137L), GARP, CSF-1R, A2AR, CD73, CD47, tryptophan 2,3-dioxygenase (TDO) or indoleamine 2,3 dioxygenase (IDO).

Terms

In order that the present disclosure may be more readily understood, certain terms are first defined. As used in this application, except as otherwise expressly provided herein, each of the following terms shall have the meaning set forth below. Additional definitions are set forth throughout the application.

As used herein, "a", "an", "the", "at least one", and "one or more" are used interchangeably.

"Administering" refers to the physical introduction of a composition comprising an inhibitor of the present invention to a subject, using any of the various methods and delivery systems known to those skilled in the art. Preferred routes of administration for the anti-PD-1 antibody include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. A SK inhibitor of the present invention is typically administered via a non-parenteral route, preferably orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

As used herein, the term "agent" refers to a compound having a pharmacological activity—an effect of the agent on an individual. The terms "agent," "compound," and "drug" are used interchangeably herein.

"Ameliorate" refers to any reduction in the extent, severity, frequency, and/or likelihood of a symptom or clinical sign characteristic of a particular condition.

A "SK inhibitor-treated cancer cell" or an "ABC296460-treated cancer cell" of the present invention will have increased expression of calreticulin on the surface of the treated cells. Without wishing to be bound by theory, overexpression of calreticulin is believed to act as at least one of the neoantigens that promote an immune response. Surface expression of calreticulin could be measured by flow cytometry of cells prior to injection, and the cells could even be sorted into a subset that has high expression of calreticulin to optimize the immune response. A SK inhibitor-treated cancer cell or an ABC294640-treated cancer cell prepared by the methods disclosed herein are particularly effective in eliciting an anticancer immune response.

Calreticulin also known as calregulin, CRP55, CaBP3, calsequestrin-like protein, and endoplasmic reticulum resident protein 60 (ERp60) is a multifunctional soluble protein that binds $Ca^{2+}$ ions (a second messenger in signal transduction), rendering it inactive.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $Y_H$) and a heavy chain constant region. The heavy chain constant region comprises three constant domains, Cm, Cm and m—Each light chain comprises a light chain variable region (abbreviated herein as YL) and a light chain constant region. The light chain constant region comprises one constant domain, CL. The $V_\#$ and YL regions can be further subdivided into regions of hypervariability, termed complementarity determining regions (CDRs), interspersed with regions that are more conserved, termed framework regions (FR). Each $Y_H$ and YL comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

"Antibody fragment" refers to a sub-portion of an antibody that retains at least some of the binding function of the parent antibody toward a ligand.

"Antibody derivative" refers to a chemically modified version of an antibody or antibody fragment. Some examples of derivatives include attachment to other functional molecules such a PEG groups, peptides, proteins or other antibodies.

The term "immunogenic cell death" ("ICD") is any type of cell death eliciting an immune response. ICD involves changes in the composition of the cell surface.

A concentration of SK inhibitor, for example compound ABC294640 "known to cause immunogenic cell death in vitro" means a toxic amount of the compound selected to cause at least 75% killing of the tumor cells. In an embodiment, a concentration of SK inhibitor, for example ABC294640 known to cause cell death in vitro is from about 10 μM to about 100 μM; from about 20 μM to about 60 μM; from about 25 μM to about 55 μM; from about 30 μM to about 50 μM; from about 35 μM to about 45 μM. In an embodiment, a concentration of SK inhibitor, for example ABC294640 known to cause immunogenic cell death in vitro is 40 μM.

An "Ex vivo" method disclosed herein means that cells taken from a patient are treated with a compound that modifies sphingolipid metabolism in vitro and then primed so that they can be returned to the patient's body.

The term "monoclonal antibody" ("mAb") refers to a non-naturally occurring preparation of antibody molecules of single molecular composition, i.e., antibody molecules whose primary sequences are essentially identical, and which exhibits a single binding specificity and affinity for a particular epitope. A monoclonal antibody is an example of an isolated antibody. MAbs may be produced by hybridoma, recombinant, transgenic or other techniques known to those skilled in the art.

Monoclonal antibodies, antibody fragments, and antibody derivatives for blocking immune checkpoint pathways can be prepared by any of several methods known to those of ordinary skill in the art, including but not limited to, somatic cell hybridization techniques and hybridoma, methods. Hybridoma generation is described in Antibodies, A Laboratory Manual, Harlow and Lane, 1988, Cold Spring Harbor Publications, New York. Human monoclonal antibodies can be identified and isolated by screening phage display libraries of human immunoglobulin genes by methods described for example in U.S. Pat. Nos. 5,223,409, 5,403,484, 5,571,698, 6,582,915, and 6,593,081. Monoclonal antibodies can be prepared using the general methods described in U.S. Pat. No. 6,331,415 (Cabilly).

"Neoantigens" are unique molecules or proteins that help immune cells identify and fight cancer cells. In an embodiment, in vitro treatment of patient-derived cancer cells with a toxic concentration of SK inhibitor, for example ABC294640 results in overexpression of calreticulin on the surface of the treated cancer cells. These treated ("primed") cancer cells can then be administered to the patient to help fight/treat the cancer.

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies and are used synonymously. As an example, human monoclonal antibodies can be prepared using a XenoMouse™ (Abgenix, Freemont, Calif.) or hybridomas of B cells from a XenoMouse. A XenoMouse is a murine host having functional human immunoglobulin genes as described in U.S. Pat. No. 6,162,963 (Kucherlapati).

A "humanized antibody" refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen" antibody refers to an antibody that binds specifically to the antigen. For example, an anti-PD-1 antibody binds specifically to PD-1 and an anti-CTLA-4 antibody binds specifically to CTLA-4.

"Block", "blocking", "blockade" and variations thereof have the same meaning as "inhibit", "inhibiting", "inhibition" and variations thereof. The term "blockade" is meant to encompass both partial and complete blockade.

"Cell-mediated immune activity" refers to a biological activity considered part of a cell-mediated immune response such as, for example, an increase in the production of at least one $T_{H1}$ cytokine.

"Checkpoint inhibitors" or "Immune checkpoint inhibitors" include any agent that enhances the immune system or immune responses. Such inhibitors may include small molecules, peptides, polypeptides, proteins, antibodies, antibody fragments, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ (αβ.) T cells), CD160 (also referred to as BY55), CGEN-15049, CHK 1 and CHK2 kinases, A2aR and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics or small molecules, that bind to and block or inhibit the activity of one or more of CTLA-4, PDL1, PDL2, PD1, BTLA, HVEM, TIM3, GAL9, LAG3, VISTA, KIR, 2B4, CD160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor). Checkpoint protein ligands include, but are not limited to PD-L1, PD-L2, B7-H3, B7-H4, CD28, CD86 and TIM-3.

"Immune cell" refers to cell of the immune system, i.e., a cell directly or indirectly involved in the generation or maintenance of an immune response, whether the immune response is innate, acquired, humoral, or cell-mediated.

"Induce" and variations thereof refer to any measurable increase in cellular activity. For example, induction of an immune response may include, for example, an increase in the production of a cytokine, activation, proliferation, or maturation of a population of immune cells, and/or other indicator of increased immune function.

"Subject" or "Patient" as used herein are synonymous and refer to a human adult, child, or infant.

Programmed death-1 (PD-1) is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1, CD274, B7-H1) and Programmed Death Ligand-2 (PD-L2, CD273, B7-DC). PD-L1 and PD-L2 downregulate T cell activation and cytokine secretion upon binding to PD-1, that are expressed on antigen-presenting cells as well as many human cancers and have been shown to downregulate T cell activation and cytokine secretion upon binding to PD-1. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863. Inhibition of the PD-1/PD-L1 interaction mediates potent antitumor activity in preclinical models (U.S. Pat. Nos. 8,008,449 and 7,943,743), and the use of antibody inhibitors of the PD-1/PD-L1 interaction for treating cancer has entered clinical trials (Brahmer et al, 2010; Topalian et al, 2012a; Topalian et al, 2014; Hamid et al., 2013; Brahmer et al, 2012; Flies et al, 2011; Pardoll, 2012; Hamid and Carvajal, 2013).

Blockade of the PD-1/PD-L1 ligation using antibodies to PD-L1 has been shown to restore and augment T cell activation in many systems. Patients with advanced cancer benefit from therapy with a monoclonal antibody to PD-L1. Preclinical animal models of tumors and chronic infections have shown that blockade of the PD-1/PD-L1 pathway by monoclonal antibodies can enhance the immune response and result in tumor rejection or control of infection. Antitumor immunotherapy via PD-1/PD-L1 blockade may augment therapeutic immune response to a number of histologically distinct tumors.

Examples of PD-1/PD-L1 inhibitors currently on the market in the US includes pembrolizumab (Keytruda®, Merck), nivolumab (Opdivo®, Bristol-Myers Squibb), atezolizumab (Tecentriq®, Roche), avelumab (Bavencio®, EMD and Pfizer), and durmalumab (Imfinzi®, AstraZeneca). Any of these PD-1/PD-L1 inhibitors can be used in conjunction with a SK inhibitor of the present invention.

Nivolumab (formerly designated 5C4, BMS-936558, MDX-1 106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014). Nivolumab has shown activity in a variety of advanced solid tumors, including renal cell carcinoma (renal adenocarcinoma, or hypernephroma), melanoma, and non-small cell lung cancer (NSCLC) (Topalian et al, 2012a; Topalian et al., 2014; Drake et al, 2013; WO 2013/173223).

Ipilimumab (YERVOY®) was the first checkpoint antibody approved by the FDA in 2011 and is a fully human, IgG1 monoclonal antibody that blocks the binding of CTLA-4 to its B7 ligands, thereby stimulating T cell activation and improving overall survival (OS) in patients with advanced melanoma (Hodi et al, 2010) as disclosed in U.S. Pat. No. 6,984,720. Ipilimumab is approved for the treatment of melanoma at 3 mg/kg given intravenously once every 3 weeks for 4 doses. Thus, in preferred embodiments, 3 mg/kg is the highest dosage of ipilimumab used in combination with the anti-PD-1 antibody though, in certain embodiments, an anti-CTLA-4 antibody such as ipilimumab may be dosed within the range of about 0.3-10 mg/kg body weight every two or three weeks when combined with nivolumab. A dosage of ipilimumab that is significantly lower than the approved 3 mg/kg every 3 weeks, for instance 0.3 mg/kg or less every 3 or 4 weeks, is regarded as a subtherapeutic dosage. It has been shown that combination dosing of nivolumab at 3 mg/kg and ipilimumab at 3 mg/kg exceeded the MTD in a melanoma population, whereas a combination of nivolumab at 1 mg/kg plus ipilimumab at 3 mg/kg or nivolumab at 3 mg/kg plus ipilimumab at 1 mg/kg was found to be tolerable in melanoma patients (Wolchok et al., 2013). Accordingly, although nivolumab is tolerated up to 10 mg/kg given intravenously every 2 weeks, in preferred embodiments doses of the anti-PD-1 antibody do not exceed 3 mg/kg when combined with ipilimumab. In certain embodiments, based on risk-benefit and PK-PD assessments, the dosage used comprises a combination of nivolumab at 1 mg/kg plus ipilimumab at 3 mg/kg, nivolumab at 3 mg/kg plus ipilimumab at 1 mg/kg, or nivolumab at 3 mg/kg plus ipilimumab at 3 mg/kg is used, each administered at a dosing frequency of once every 2-4 weeks, preferably once every 3 weeks. In certain other embodiments, nivolumab is administered at a dosage of 0.1, 0.3, 1, 2, 3 or 5 mg/kg in combination with ipilimumab administered at a dosage of 0.1, 0.3, 1, 2, 3 or 5 mg/kg, once every 2 weeks, once every 3 weeks, or once every 4 weeks.

As used herein, the term "PD-1 antibodies" refers to antibodies that antagonize the activity and/or proliferation of lymphocytes by agonizing PD-1. The term "antagonize the activity" relates to a decrease (or reduction) in lymphocyte proliferation or activity that is at least 5%, 10%, 20%, 30%, 40%, 50%, 60%, 70%, 80%, 90%, or more. The term "antagonize" may be used interchangeably with the terms "inhibitory" and "inhibit". PD-1-mediated activity can be determined quantitatively using T cell proliferation assays as described herein.

"Pharmaceutically acceptable formulations" can deliver therapeutically effective amounts of the compounds of the disclosure to a subject by a chosen route of administration, are generally tolerated by the subject, and have an acceptable toxicity profile (preferably minimal to no toxicity at an administered dose). Suitable pharmaceutically acceptable formulations are described in Remington's Pharmaceutical Sciences, 18th Edition (1990), Mack Publishing Co. and can be readily selected by one of ordinary skill in the art.

"Pharmaceutically acceptable salt" refers to a derivative of a compound in which the compound is modified by converting at least one acid or base group in the compound to a non-toxic salt form. Examples of "pharmaceutically acceptable salts are described by Berge in Journal of Pharmaceutical Science (1977), 66, pages 1-19, and include acid addition salts and base addition salts. Acid addition salts include mineral or organic acid salts of basic moieties in a compound (such as amine groups). Suitable acid addition salts include those derived from inorganic acids such as for example hydrochloric acid, hydrobromic acid, sulfuric acid, nitric acid, and the like. Suitable acid addition salts derived from organic acids such as mono- and di-carboxylic acids (e.g., acetic acid, propionic acid), hydroxyalkonic acids (e.g., citric acid, tartaric acid), aromatic acids (e.g., benzoic acid, xinofoic acid, pamoic acid), aliphatic and aromatic sulfonic acids (e.g., para-toluene sulfonic acid), and the like. Base addition salts include alkaline earth mineral salts and organic amine salts of acidic moieties in a compound (such as carboxylic acid groups). Suitable base addition salts include sodium, potassium, magnesium, calcium salts, and the like. Additional suitable base addition salts include non-toxic organic amines such as choline, ethylenediamine, and the like.

As used herein, the term "a suitable period of time" refers to the period of time starting when a subject begins treatment for a diagnosis of cancer using a method of the present disclosure, throughout the treatment, and up until when the subject stops treatment. In an embodiment, a suitable period of time is one (1) week. In an embodiment, a suitable period of time is between one (1) week and two (2) weeks. In an embodiment, a suitable period of time is two (2) weeks. In an embodiment, a suitable period of time is between two (2) weeks and three (3) weeks. In an embodiment, a suitable period of time is three (3) weeks. In an embodiment, a suitable period of time is between three (3) weeks and four (4) weeks. In an embodiment, a suitable period of time is four (4) weeks. In an embodiment, a suitable period of time is between four (4) weeks and five (5) weeks. In an embodiment, a suitable period of time is five (5) weeks. In an embodiment, a suitable period of time is between five (5) weeks and six (6) weeks. In an embodiment, a suitable period of time is six (6) weeks. In an embodiment, a suitable period of time is between six (6) weeks and seven (7) weeks. In an embodiment, a suitable period of time is seven (7) weeks. In an embodiment, a suitable period of time is between seven (7) weeks and eight (8) weeks. In an embodiment, a suitable period of time is eight (8) weeks. In an embodiment, a suitable period of time is at least two months, three months, four months, five months, six months, seven months, eight months, nine months, ten months, eleven months, twelve months. In an embodiment, a suitable period of time is at least one year.

As used herein, the term "synergistic" refers to the coordinated or correlated action of two or more agents of the present invention so that the combined action is greater than the sum of each acting separately. In an embodiment, agents of the present invention, when administered together as part of a treatment regimen, provide a therapeutic synergy without accompanying synergistic side effects (e.g., but not limited to, cross-reacting agents).

A "therapeutically effective amount" or "therapeutically effective dosage" is an amount that ameliorates at least one symptom or clinical sign of a tumor. Ameliorating at least one symptom or clinical sign of a tumor can include a decrease in the size of a tumor, stabilization in the size or growth of a tumor, a reduction in the rate of growth of a tumor, an increase in tumor necrosis, a change in the tumor structure such as disintegration, a change in a biochemical marker associated with decrease in tumor establishment, a decrease in tumor progression or a decrease in tumor survival.

As used herein, "treating a cancer", "treating", and "treatment" includes, but is not limited to, preventing or reducing the development of a cancer, reducing the symptoms of cancer, suppressing or inhibiting the growth of an established cancer, preventing metastasis and/or invasion of an existing cancer, promoting or inducing regression of the cancer, inhibiting or suppressing the proliferation of cancerous cells, reducing angiogenesis, killing of malignant or cancerous tumor cells, or increasing the amount of apoptotic cancer cells.

A "patient in need of treatment", as used herein, means a patient that is identified as being in need of treatment. For instance, a patient in need of cancer treatment is a patient identified as having cancer or being at risk for developing cancer. A patient may be diagnosed as being in need of treatment by a healthcare professional and/or by performing one or more diagnostic assays. For instance, patient in need of cancer treatment may be a patient diagnosed with cancer or being at risk of cancer by a healthcare professional. Diagnostic assays to evaluate if a patient has a cancer or is at risk for developing cancer are known in the art.

The use of the term "flat dose" with regard to the methods and dosages of the invention means a dose that is administered to a patient without regard for the weight or body surface area (BSA) of the patient. The flat dose is therefore not provided as a mg/kg dose, but rather as an absolute amount of the agent (e.g., the anti-PD-1 antibody). For example, a 60 kg person and a 100 kg person would receive the same dose of an antibody (e.g., 240 mg of an anti-PD1 antibody).

The term "weight based dose" as referred to herein means that a dose that is administered to a patient is calculated based on the weight of the patient. For example, when a patient with 60 kg body weight requires 3 mg/kg of an anti-PD-1 antibody, one can calculate and use the appropriate amount of the anti-PD-1 antibody (i.e., 180 mg) for administration.

An increase in at least one cell-mediated immune response of a cell population that includes cells of a tumor refers to an increase in at least one biochemical, histological, or immunological marker associated with improvement of the immunological profile of the tumor microenvironment. Markers in which an increase in the amount of the marker is associated with an improvement of the immunological profile of the tumor microenvironment include, but are not limited to, interferon-alpha; interferon-gamma; interferon inducible proteins; TNF-alpha; chemokines such as CCL2, CCL3, CCL4, CXCL2; activated T-cells; activated B-cells; activated NK-cells; tumor specific T-cells, activated tumor associated macrophages; chemokine receptors such as CCR6; or tumor associated lymphoid aggregates.

Markers associated with a tumor microenvironment can be determined, for example, by analysis of a biopsy (for example needle biopsy) from the tumor, the localized tumor region, or a tumor draining lymph node. Analysis for the markers can be done using standard techniques such as by histology (H&E stain), flow cytometry, gene expression assays (quantitative PCR), immunochemistry techniques, as well as other techniques commonly known to those of ordinary skill in the art.

The term "in vitro" as used herein refers to procedures performed in an artificial environment, such as for example, without limitation, in a test tube or cell culture system. The skilled artisan will understand that, for example, an isolate SK enzyme may be contacted with a modulator in an in vitro environment. Alternatively, an isolated cell may be contacted with a modulator in an in vitro environment.

The term "in vivo" as used herein refers to procedures performed within a living organism such as, without limitation, a human, monkey, mouse, rat, rabbit, bovine, equine, porcine, canine, feline, or primate.

Active ingredients or agents useful in the invention include those described herein in any of their pharmaceutically acceptable forms, including isomers, salts, solvates, and polymorphs thereof, as well as racemic mixtures and prodrugs.

Inhibitors of Sphingosine Kinase of the Present Disclosure

Sphingosine kinase (SK) is an oncogenic sphingolipid-metabolizing enzyme that catalyzes the formation of the mitogenic second messenger sphingosine-1-phosphate (S1P) at the expense of proapoptotic ceramide. Thus, SK is an attractive target for cancer therapy because blockage of S1P leads to inhibition of proliferation, as well as the induction of apoptosis in cancer cells. This disclosure provides aryladamantane compounds that inhibit SK. In an embodiment, the SK inhibitor is a selective inhibitor of sphingosine kinase-1 (SK1). In an embodiment, the SK inhibitor is a selective inhibitor of sphingosine kinase-2 (SK2). In an embodiment, the SK inhibitor is a dual inhibitor of sphingosine kinase (inhibits both sphingosine kinase-1 and sphingosine kinase-2.

Examples of aryladamantane compounds of the present invention that are inhibitors of SK are generally represented by Formula 1, shown below:

(I)

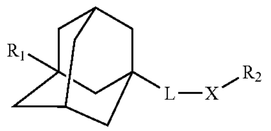

and pharmaceutically acceptable salts thereof, wherein:

L is a bond or is —C($R_3$,$R_4$)—;

X is —C($R_3$,$R_4$)N($R_5$)—, —C(O)N($R_4$)—, —N($R_4$)C(O)—, —C($R_4$,$R_5$)—, —N($R_4$)—, —O—, —S—, —C(O)—, —S(O)$_2$—, —S(O)$_2$N($R_4$)— or —N($R_4$)S(O)$_2$—;

$R_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —$NO_2$, —$NH_2$, —$CO_2$ (alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

$R_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —$NO_2$, —$NH_2$, —$CO_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —C(O)—NH-aryl, -alkenyl-heteroaryl, —C(O)-heteroaryl, or -alkenyl-heteroaryl-aryl;

$R_3$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, oxo (═O), —COOH, —OH, —SH, —S-alkyl, —CN, —$NO_2$, —$NH_2$, —$CO_2$ (alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

wherein the alkyl and ring portion of each of the above $R_1$, $R_2$, and $R_3$ groups is optionally substituted with up to 5 groups that are independently ($C_1$-$C_6$)alkyl, halogen, haloalkyl, —OC(O) ($C_1$-$C_6$ alkyl), —C(O)O($C_1$-$C_6$ alkyl), —CONR'R", —OC(O)NR'R", —NR'C(O)R", —$CF_3$, —$OCF_3$, —OH, $C_1$-$C_6$ alkoxy, hydroxyalkyl, —CN, —$CO_2$H, —SH, —S-alkyl, —SOR'R", —$SO_2$R', —$NO_2$, or NR'R", wherein R' and R" are independently H or ($C_1$-$C_6$) alkyl, and wherein each alkyl portion of a substituent is optionally further substituted with 1, 2, or 3 groups independently selected from halogen, CN, OH, and $NH_2$; and $R_4$ and $R_5$ are independently H or alkyl, provided that when $R_3$ and $R_4$ are on the same carbon and $R_3$ is oxo, then $R_4$ is absent.

Aryladamantane compounds of Formula I include compounds of formula I-1:

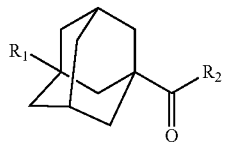
(I-1)

and pharmaceutically acceptable salts thereof, wherein:

$R_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —$NO_2$, —$NH_2$, —$CO_2$ (alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl; and $R_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —$NO_2$, —$NH_2$, —$CO_2$ (alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —NH-aryl, -alkenyl-heteroaryl, -heteroaryl, —NH-alkyl, —NH-cycloalkyl, or -alkenyl-heteroaryl-aryl, wherein the alkyl and ring portion of each of the above $R_1$, and $R_2$ groups is optionally substituted with up to 5 groups that are independently ($C_1$-$C_6$)alkyl, halogen, haloalkyl, —OC(O) ($C_1$-$C_6$ alkyl), —C(O)O($C_1$-$C_6$ alkyl), —CONR'R", —OC(O)NR'R", —NR'C(O)R", —$CF_3$, —$OCF_3$, —OH, $C_1$-$C_6$ alkoxy, hydroxyalkyl, —CN, —$CO_2$H, —SH, —S-alkyl, —SOR'R", —$SO_2$R', —$NO_2$, or NR'R", wherein R' and R" are independently H or ($C_1$-$C_6$)alkyl, and wherein each alkyl portion of a substituent is optionally further substituted with 1, 2, or 3 groups independently selected from halogen, CN, OH, $NH_2$.

Aryladamantane compounds of Formula I include those of formula II:

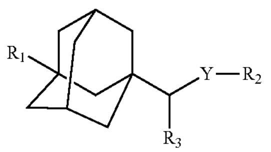
(II)

and pharmaceutically acceptable salts thereof, wherein:

Y is —C($R_4$,$R_5$)—, —N($R_4$), —O—, or —C(O)—;

$R_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —$NO_2$, —$NH_2$, —$CO_2$ (alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

$R_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —$NO_2$, —$NH_2$, —$CO_2$ (alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —C(O)—NH-aryl, -alkenyl-heteroaryl, —C(O)-heteroaryl, or -alkenyl-heteroaryl-aryl;

$R_3$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, oxo (═O), —COOH, —OH, —SH, —S-alkyl, —CN, —$NO_2$, —$NH_2$, —$CO_2$ (alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

wherein the alkyl and ring portion of each of the above $R_1$, $R_2$, and $R_3$ groups is optionally substituted with up to 5 groups that are independently ($C_1$-$C_6$)alkyl, halogen, haloalkyl, —OC(O) ($C_1$-$C_6$ alkyl), —C(O)O($C_1$-$C_6$ alkyl), —CONR'R", —OC(O)NR'R", —NR'C(O)R", —$CF_3$, —$OCF_3$, —OH, $C_1$-$C_6$ alkoxy, hydroxyalkyl, —CN, —$CO_2$H, —SH, —S-alkyl, —SOR'R", —SOR', —$NO_2$, or NR'R", wherein R' and R" are independently H or ($C_1$-$C_6$)alkyl, and wherein each alkyl portion of a substituent is optionally further substituted with 1, 2, or 3 groups independently selected from halogen, CN, OH, $NH_2$; and $R_4$ and $R_5$ are independently H or alkyl.

Compounds of the formula II include those wherein:

Y is —C($R_4$,$R_5$)— or —N($R_4$)—;

$R_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —$NO_2$, —$NH_2$, —$CO_2$ (alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

$R_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —$NO_2$, —$NH_2$, —$CO_2$ (alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —C(O)—NH-aryl, -alkenyl-heteroaryl, —C(O)-heteroaryl, or -alkenyl-heteroaryl-aryl;

wherein the alkyl and ring portion of each of the above $R_1$ and $R_2$ groups is optionally substituted with up to 5 groups that are independently ($C_1$-$C_6$)alkyl, halogen, haloalkyl, —OC(O) ($C_1$-$C_6$ alkyl), —C(O)O($C_1$-$C_6$ alkyl), —CON$R_4$$R_5$, —OC(O)N$R_4$$R_5$, —N$R_4$C(O)$R_5$, —$CF_3$, —O$CF_3$, —OH, $C_1$-$C_6$ alkoxy, hydroxyalkyl, —CN, —$CO_2$H, —SH, —S-alkyl, —SO$R_4$$R_5$, —$SO_2$$R_4$$R_5$, —$NO_2$, or N$R_4$$R_5$, and wherein each alkyl portion of a substituent is optionally further substituted with 1, 2, or 3 groups independently selected from halogen, CN, OH, $NH_2$;

$R_3$ is H, alkyl, or oxo (═O); and $R_4$ and $R_5$ are independently H or ($C_1$-$C_6$)alkyl.

A particularly preferred aryladamantane SK inhibitor compound of the present invention is illustrated below and referred to as ABC294640 [3-(4-chlorophenyl)-adamantane-1-carboxylic acid (pyridin-4-ylmethyl)amide]:

ABC294640

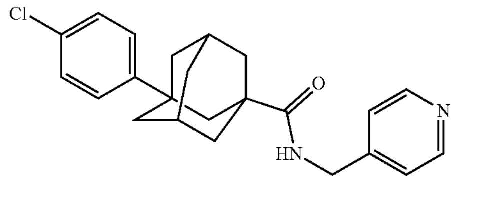

The precise amount of SK inhibitor incorporated in a particular method or therapeutic combination of the disclosure may vary according to factors known in art such as for example, the physical and clinical status of the subject, the method of administration, the content of the formulation, the intended dosing regimen or sequence. Accordingly, it is not practical to specifically set forth an amount that constitutes an amount of SK inhibitor therapeutically effective for all possible applications. Those of ordinary skill in the art, however, can readily determine an appropriate amount with due consideration of such factors.

Anti-PD-1 Antibodies

Human monoclonal antibodies that bind specifically to PD-1 with high affinity have been disclosed in U.S. Pat. No. 8,008,449. Other anti-PD-1 monoclonal antibodies have been described in, for example, U.S. Pat. Nos. 6,808,710, 7,488,802, 8,168,757 and 8,354,509, and PCT Publication No. WO 2012/145493. Each of the anti-PD-1 human monoclonal antibodies disclosed in U.S. Pat. No. 8,008,449 has been demonstrated to exhibit one or more of the following characteristics: (a) binds to human PD-1 with a KD of $1\times10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and (j) inhibits tumor cell growth in vivo. Anti-PD-1 antibodies usable in the present invention include monoclonal antibodies that bind specifically to human PD-1 and exhibit at least one, preferably at least five, of the preceding characteristics. A preferred anti-PD-1 antibody is nivolumab. Another preferred anti-PD-1 antibody is pembrolizumab.

Anti-PD-1 antibodies usable in the disclosed methods also include isolated antibodies that bind specifically to human PD-1 and cross-compete for binding to human PD-1 with nivolumab (see, e.g. U.S. Pat. No. 8,008,449; WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of nivolumab by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 as, nivolumab are monoclonal antibodies. For administration to human subjects, these cross-competing antibodies are preferably chimeric antibodies, or more preferably humanized or human antibodies. Such chimeric, humanized or human monoclonal antibodies can be prepared and isolated by methods well known in the art.

Anti-PD-1 antibodies usable in the methods of the disclosed invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $_{L}$, $_{H}$, $C_L$ and Cm domains; (ii) a F(ab')$_2$ fragment, a bivalent fragment comprising two Fab fragments linked by a disulfide bridge at the hinge region; (iii) a Fd fragment consisting of the $V_{\#}$ and C domains; and (iv) a Fv fragment consisting of the Vi and $V_{\#}$ domains of a single arm of an antibody.

Anti-CTLA-4 antibodies of the instant invention bind to human CTLA-4 so as to disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing or prolonging an immune response.

Human monoclonal antibodies that bind specifically to CTLA-4 with high affinity have been disclosed in U.S. Pat. Nos. 6,984,720 and 7,605,238. Other anti-PD-1 monoclonal antibodies have been described in, for example, U.S. Pat. Nos. 5,977,318, 6,051,227, 6,682,736, and 7,034,121. The anti-PD-1 human monoclonal antibodies disclosed in U.S. Pat. Nos. 6,984,720 and 7,605,238 have been demonstrated to exhibit one or more of the following characteristics: (a) binds specifically to human CTLA-4 with a binding affinity reflected by an equilibrium association constant ($K_a$) of at least about $10^7$ M$^{'1}$, or about $10^9$ M$^{'1}$, or about $10^{10}$ M$^{''1}$ to $10^{11}$ M$^{'1}$ or higher, as determined by Biacore analysis; (b) a kinetic association constant ($k_a$) of at least about $10^3$, about $10^4$, or about $10^5$ m$^{'1}$ s$^{'1}$; (c) a kinetic disassociation constant ($k^{\wedge}$) of at least about $10^3$, about $10^4$, or about $10^5$ m$^{''1}$ s$^{''1}$; and (d) inhibits the binding of CTLA-4 to B7-1 (CD80) and B7-2 (CD86). Anti-CTLA-4 antibodies usable in the present invention include monoclonal antibodies that bind specifically to human CTLA-4 and exhibit at least one, and preferably at least three of the preceding characteristics.

Anti-CTLA-4 antibodies usable in the disclosed methods also include isolated antibodies that bind specifically to human PD-1 and cross-compete for binding to human CTLA-4 with ipilimumab or tremelimumab or bind to the same epitope region of human CTLA-4 as ipilimumab or tremelimumab. In certain preferred embodiments, the antibodies that cross-compete for binding to human CTLA-4 with, or bind to the same epitope region of human PD-1 as does ipilimumab or tremelimumab, are antibodies comprising a heavy chain of the human IgG1 isotype. For administration to human subjects, these cross-competing antibodies are preferably chimeric antibodies, or more preferably humanized or human antibodies. Usable anti-CTLA-4 antibodies also include antigen-binding portions of the above antibodies such as Fab, F(ab') 2, Fd, or Fv fragments.

In one specific embodiment, the present invention covers the use of a specific class of checkpoint inhibitor drugs that inhibit the activity of Cytotoxic T-Lymphocyte Antigen-4 (CTLA-4). Suitable anti-CTLA4 antagonist agents for use in the methods of the invention, include, without limitation, anti-CTLA4 antibodies, human anti-CTLA4 antibodies, mouse anti-CTLA4 antibodies, mammalian anti-CTLA4 antibodies, humanized anti-CTLA4 antibodies, monoclonal anti-CTLA4 antibodies, polyclonal anti-CTLA4 antibodies, chimeric anti-CTLA4 antibodies, MDX-010 (ipilimumab), tremelimumab, anti-CD28 antibodies, anti-CTLA4 adnectins, anti-CTLA4 domain antibodies, single chain anti-CTLA4 fragments, heavy chain anti-CTLA4 fragments, light chain anti-CTLA4 fragments, inhibitors of CTLA4 that agonize the co-stimulatory pathway, the antibodies disclosed in PCT Publication No. WO2001/014424, the antibodies disclosed in PCT Publication No. WO2004/035607, the antibodies disclosed in U.S. Publication No. 2005/0201994, and the antibodies disclosed in granted European Patent No. EP1212422 B1. Additional CTLA-4 antibodies are described in U.S. Pat. Nos. 5,811,097, 5,855,887, 6,051,227, and 6,984,720; in PCT Publication Nos. WO01/14424 and WO00/37504; and in U.S. Publication Nos. 2002/0039581 and 2002/086014. Other anti-CTLA-4 antibodies that can be used in a method of the present invention include, for example, those disclosed in: WO98/42752; U.S. Pat. Nos. 6,682,736 and 6,207,156; Hurwitz et al., Proc. Natl. Acad. Sci. USA, 95 (17): 10067-10071 (1998); Camacho et al., J. Clin. Oncology, 22 (145): Abstract No. 2505 (2004) (antibody CP-675206); Mokyr et al., Cancer Res., 58:5301-5304 (1998), and U.S. Pat. Nos. 5,977,318, 6,682,736, 7,109,003, and 7,132,281.

Additional anti-CTLA4 antagonists include, but are not limited to, the following: any inhibitor that is capable of disrupting the ability of CD28 antigen to bind to its cognate ligand, to inhibit the ability of CTLA4 to bind to its cognate ligand, to augment T cell responses via the co-stimulatory pathway, to disrupt the ability of B7 to bind to CD28 and/or CTLA4, to disrupt the ability of B7 to activate the co-stimulatory pathway, to disrupt the ability of CD80 to bind to CD28 and/or CTLA4, to disrupt the ability of CD80 to activate the co-stimulatory pathway, to disrupt the ability of CD86 to bind to CD28 and/or CTLA4, to disrupt the ability of CD86 to activate the co-stimulatory pathway, and to disrupt the co-stimulatory pathway, in general from being activated. This necessarily includes small molecule inhibitors of CD28, CD80, CD86, CTLA4, among other members of the co-stimulatory pathway; antibodies directed to CD28, CD80, CD86, CTLA4, among other members of the co-stimulatory pathway; antisense molecules directed against CD28, CD80, CD86, CTLA4, among other members of the co-stimulatory pathway; adnectins directed against CD28, CD80, CD86, CTLA4, among other members of the co-stimulatory pathway, RNAi inhibitors (both single and double stranded) of CD28, CD80, CD86, CTLA4, among other members of the co-stimulatory pathway, among other anti-CTLA4 antagonists.

In some embodiments of the present disclosure, the immune checkpoint inhibitor compound inhibits the signaling interaction between an immune checkpoint receptor and the corresponding ligand of the immune checkpoint receptor. The immune checkpoint inhibitor compound can act by blocking activation of the immune checkpoint pathway by inhibition (anatagonism) of an immune checkpoint receptor (some examples of receptors include CTLA-4, PD-1, LAG-3, TIM-3, BTLA, and KIR) or by inhibition of a ligand of an immune checkpoint receptor (some examples of ligands include PD-L1 and PD-L2). In such embodiments, the effect of the immune checkpoint inhibitor compound is to reduce or eliminate down regulation of certain aspects of the immune system anti-tumor response in the tumor microenvironment.

The immune checkpoint receptor cytotoxic T-lymphocyte associated antigen 4 (CTLA-4) is expressed on T-cells and is involved in signaling pathways that reduce the level of T-cell activation. It is believed that CTLA-4 can downregulate T-cell activation through competitive binding and sequestration of CD80 and CD86. In addition, CTLA-4 has been shown to be involved in enhancing the immunosuppressive activity of $T_{Reg}$ cells.

In some embodiments of the present disclosure, the immune checkpoint inhibitor compound is a small organic molecule (molecular weight less than 1000 daltons), a peptide, a polypeptide, a protein, an antibody, an antibody fragment, or an antibody derivative. In some embodiments, the immune checkpoint inhibitor compound is an antibody. In some embodiments, the antibody is a monoclonal antibody, specifically a human or a humanized monoclonal antibody.

Methods for the preparation and us of immune checkpoint antibodies are described in the following illustrative publications. The preparation and therapeutic uses of anti-CTLA-4 antibodies are described in U.S. Pat. No. 7,229,628 (Allison), U.S. Pat. No. 7,311,910 (Linsley), and U.S. Pat. No. 8,017,144 (Korman). The preparation and therapeutic uses of anti-PD-1 antibodies are described in U.S. Pat. No. 8,008,449 (Korman) and U.S. Pat. No. 8,552,154 (Freeman). The preparation and therapeutic uses of anti-PD-L1 antibodies are described in U.S. Pat. No. 7,943,743 (Korman). The preparation and therapeutic uses of anti-TIM-3 antibodies are described in U.S. Pat. No. 8,101,176 (Kuchroo) and U.S. Pat. No. 8,552,156 (Tagayanagi). The preparation and therapeutic uses of anti-LAG-3 antibodies are described in U.S. Patent Application No. 2011/0150892 (Thudium) and International Publication Number WO2014/008218 (Lonberg). The preparation and therapeutic uses of anti-KIR antibodies are described in U.S. Pat. No. 8,119,775 (Moretta). The preparation of antibodies that block BTLA regulated inhibitory pathways (anti-BTLA antibodies) are described in U.S. Pat. No. 8,563,694 (Mataraza).

In some embodiments of the present disclosure, the immune checkpoint inhibitor compound is a CTLA-4 receptor inhibitor, a PD-1 receptor inhibitor, a LAG-3 receptor inhibitor, a TIM-3 receptor inhibitor, a BTLA receptor inhibitor, or a KIR receptor inhibitor. In some embodiments, the immune checkpoint inhibitor compound is an inhibitor of PD-L1 or an inhibitor of PD-L2.

Any suitable daily dose of a checkpoint inhibitor is contemplated for use with the compositions, dosage forms, and methods disclosed herein. Daily dose of the checkpoint inhibitor depends on multiple factors, the determination of which is within the skills of one of skill in the art. For example, the daily dose of the checkpoint inhibitor depends on the strength of the checkpoint inhibitor. Weak immune checkpoint inhibitors will require higher daily doses than moderate immune checkpoint inhibitors, and moderate immune checkpoint inhibitors will require higher daily doses than strong immune checkpoint inhibitors. For example, Merck's pembrolizumab (Keytruda) is approved for 2 mg/kg iv over 30 minutes every three weeks (50 mg lyophilized power). Nivolumab (OPDVO) is administered 3 mg/kg iv over 60 minutes every 2 weeks (injection dosage form: 40 mg/4 ml and 100 mg/10/ml in single use vial). Ipilimumab (YERVOY) is administered 3 mg/kg iv over 90 minutes every 3 weeks for a total of 4 doses (dosage form: 50 mg/10 ml, 200 mg/40 ml).

Solid forms for oral administration may contain pharmaceutically acceptable binders, sweeteners, disintegrating agents, diluents, flavorings, coating agents, preservatives, lubricants, and/or time delay agents. Suitable binders include gum acacia, gelatin, corn starch, gum tragacanth, sodium alginate, carboxymethylcellulose or polyethylene glycol (PEG). Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavoring agents include peppermint oil, oil of wintergreen, cherry, orange, or raspberry flavoring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The compositions and methods of the invention can include formulation(s) of compound(s) that, upon administration to a subject, result in a concentration of the compound(s) that treats a filovirus-mediated disease. The compound(s) may be contained in any appropriate amount in any suitable carrier substance, and are generally present in an amount of 1-95% by weight of the total weight of the composition. The composition may be provided in a dosage form that is suitable for the oral, parenteral (e.g., intravenously or intramuscularly), rectal, dermatological, cutaneous, nasal, vaginal, inhalant, skin (patch), ocular, intrathecal, or intracranial administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice.

Pharmaceutical compositions according to the invention or used in the methods of the invention may be formulated to release the active compound immediately upon administration or at any predetermined time or time period after administration. The latter types of compositions are generally known as controlled release formulations, which include (i) formulations that create substantially constant concentrations of the agent(s) of the invention within the body over an extended period of time; (ii) formulations that after a predetermined lag time create substantially constant concentrations of the agent(s) of the invention within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s) (sawtooth kinetic pattern); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the combination to a particular target cell type.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound(s) are formulated with appropriate excipients into a pharmaceutical composition that, upon administration, releases the compound(s) in a controlled manner. Examples include single or multiple unit tablet or capsule compositions, oil solutions, suspensions, emulsions, microcapsules, molecular complexes, microspheres, nanoparticles, patches, and liposomes.

It is not intended that administration of compounds be limited to a single formulation and delivery method for all compounds of a combination. The combination can be administered using separate formulations and/or delivery methods for each compound of the combination using, for example, any of the above-described formulations and methods. In one example, a first agent is delivered orally, and a second agent is delivered intravenously.

The dosage of a compound or a combination of compounds depends on several factors, including: the administration method, the type of disease to be treated, the severity of the infection, whether administration first occurs at an early or late stage of infection, and the age, weight, and health of the patient to be treated. For combinations that include a synergistic pair of agents identified herein, the recommended dosage for the anti-viral agent can be less than or equal to the recommended dose as given in the Physician's Desk Reference, $69^{th}$ Edition (2015).

As described above, the compound(s) in question may be administered orally in the form of tablets, capsules, elixirs or syrups, or rectally in the form of suppositories. Parenteral administration of a compound is suitably performed, for example, in the form of saline solutions or with the compound(s) incorporated into liposomes. In cases where the compound in itself is not sufficiently soluble to be dissolved, a solubilizer such as ethanol can be applied. The correct dosage of a compound can be determined by examining the efficacy of the compound in viral replication assays, as well as its toxicity in humans.

The agents of the invention are also useful tools in elucidating mechanistic information about the biological pathways involved in viral diseases. Such information can lead to the development of new combinations or single agents for treating, preventing, or reducing a viral disease. Methods known in the art to determine biological pathways can be used to determine the pathway, or network of pathways affected by contacting cells (e.g., primary macrophage cells) infected with a virus with the compounds of the invention. Such methods can include, analyzing cellular constituents that are expressed or repressed after contact with the compounds of the invention as compared to untreated, positive or negative control compounds, and/or new single agents and combinations, or analyzing some other activity of the cell or virus such as an enzymatic activity, nutrient uptake, and proliferation. Cellular components analyzed can include gene transcripts, and protein expression. Suitable methods can include standard biochemistry techniques, radiolabeling the compounds of the invention (e.g., $^{14}C$ or $^{3}H$ labeling), and observing the compounds binding to proteins, e.g., using 2D gels, gene expression profiling. Once identified, such compounds can be used in in vivo models (e.g., knockout or transgenic mice) to further validate the tool or develop new agents or strategies to treat viral disease.

Kits and Packages

The terms "kit" and "pharmaceutical kit" refer to a commercial kit or package comprising, in one or more suitable containers, one or more pharmaceutical compositions and instructions for their use. In one embodiment, kits comprising ABC294640 and instructions for its administration are provided. In one embodiment, kits comprising ABC294640 in combination with one or more (e.g., one, two, three, one or two, or one to three) additional therapeutic agents and instructions for their administration are provided.

In an embodiment, a checkpoint inhibitor of this disclosure is formulated into administration units which are packaged in a single packaging. The single packaging encompasses but is not limited to a bottle, a child-resistant bottle, an ampoule, and a tube. In an embodiment, a checkpoint inhibitor of this disclosure and optionally additional therapeutic agents, are formulated into administration units and every single administration unit is individually packaged in a single packaging. Such individually packaged units may contain the pharmaceutical composition in any form including but not limited to liquid form, solid form, powder form, granulate form, an effervescent powder or tablet, hard or soft capsules, emulsions, suspensions, syrup, suppositories, tablet, troches, lozenges, solution, buccal patch, thin film, oral gel, chewable tablet, chewing gum, and single-use syringes. Such individually packaged units may be combined in a package made of one or more of paper, cardboard, paperboard, metal foil and plastic foil, for example a blister pack. One or more administration units may be administered once or several times a day. One or more administration units may be administered three times a day. One or more administration units may be administered twice a day. One or more administration units may be administered on a first day and one or more administration units may be administered on the following days.

EXAMPLES

The present invention may be better understood with reference to the following examples. These examples are intended to be representative of specific embodiments of the invention, and are not intended as limiting the scope of the invention.

Example 1

Method for the synthesis of 3-(4-chloro-phenyl)-adamantane-1-carboxylic acid (pyridin-4-ylmethyl)-amide, ABC294640

As an example, a process for the synthesis of ABC294640 is described in Scheme 1. The direct bromination of adamantane-1-carboxylic acid (1) in the presence of aluminum chloride ($AlCl_3$) gave 3-bromide derivative (2) of 1 which was converted to (3) by the reaction of Friedel-Crafts reaction. 3 was reacted with thionyl chloride ($SOCl_2$) to give 3-R-substituted-1-adamantanecarbonyl chlorides 4. By reaction 4 with a substituted amine, for example, 4-aminomethylpyridin (5), in THF, (6, also represented as ABC294640) and related amide compounds were obtained.

Scheme 1.

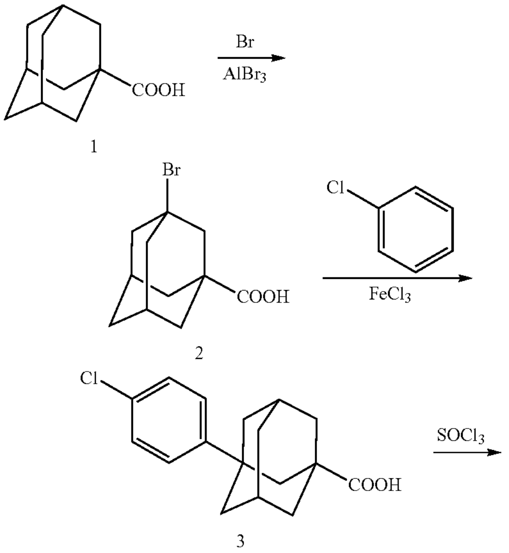

1

2

3

-continued

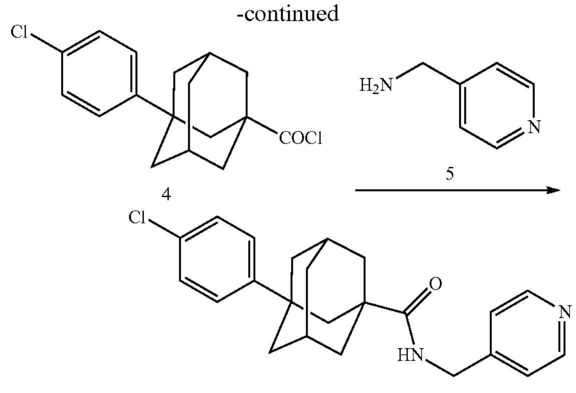

4

6

More specifically, adamantane-1-carboxylic acid (1) (45 g, 0.25 mol) was added to mixture of $AlCl_3$ (45 g, 0.34 mol) and $Br_2$ (450 g) at 0° C. and stirred at 0-10° C. for 48 hrs, kept 5 hrs at about 20° C., poured on to 500 g crushed ice, diluted with 300 ml $CHCl_3$ and decolorized with solid $Na_2S_2O_5$. The aqueous phase was extracted with $Et_2O$ (50 ml×2). The combined organic solution was washed with $H_2O$ and extracted with 10% NaOH. The alkaline extraction was acidified with 2N $H_2SO_4$ and provided 49 g (yield=75.7%) of 3-bromo-adamantane-1-carboxylic acid (2).

Over a 30 minute period, 3-bromo-adamantane-1-carboxylic acid (2) (16.0 g, 61.7 mmol) in 50 ml of dry chlorobenzene at −10° C. was added to 100 ml dry chlorobenzene and 9.3 g, 70 mmol $AlCl_3$. The mixture was then warmed to room temperature for 1 hour and then heated to 90° C. for 10 hours. The mixture was then poured onto 200 g of crushed ice, and the filtered to provide 14.2 g (yield-79.3%) of 3-(4-chloro-phenyl)-adamantane-1-carboxylic acid (3).

3 reacted with an equimolar amount of 1,1'-carbonyl diimidazole (CDI) to give intermediate 3-R-substituted-1-adamantanecarbonyl imidazole (4). By reaction of 4 with a substituted amine, the corresponding adamantylamide was obtained.

For example, reaction of 3 with 4-aminomethylpyridine (5), in toluene, produced {3-(4-Chloro-phenyl)-adamantane-1-carboxylic acid (pyridin-4-ylmethyl)-amide} (6 also represented as ABC294640) with a yield of 92.6% and a melting point of 128-130° C. 1H NMR (300 MHz, $CDCl_3$) δ 1.72-2.25 (m, 12H, Admant-CH), 4.44-4.46 (d, J=6 Hz, 2H, $CH_2$-Py), 6.18 (m, 1H, HN), 7.13-7.15 (d, J-6 Hz, 2H, H-Py), 7.15-7.30 (m, 4H, H-Ph), 8.52-8.54 (d, J=6 Hz, 2H, H-Py); $^{13}C$ NMR (300 MHz, $CDCl_3$) δ 28.98, 35.73, 36.71, 38.77, 42.18, 42.37, 44.88, 122.38, 125.30, 126.57, 128.56, 129.26, 148.39, 150.20 177.76; MS m/z (rel intensity) 381.50 ($MH^+$, 100), 383.41 (90), 384.35 (80).

Example 2

A Second Method for the Synthesis of ABC294640

A second method for the synthesis of ABC294640 and related adamantylamides is described in Scheme 2. 3-phenyl substituted intermediate (3) was prepared as described above. 3 reacted with 1,1'-carbonyldiimidazole (CDI) to give 3-R-substituted-1-adamantanecarbonylimidazole intermediate (4). By reaction of 4 with a substituted amine, for example 4-aminomethylpyridine 5, in toluene, 6 {3-(4-Chloro-phenyl)-adamantane-1-carboxylic acid (pyridin-4-ylmethyl)-amide} was obtained.

Scheme 2.

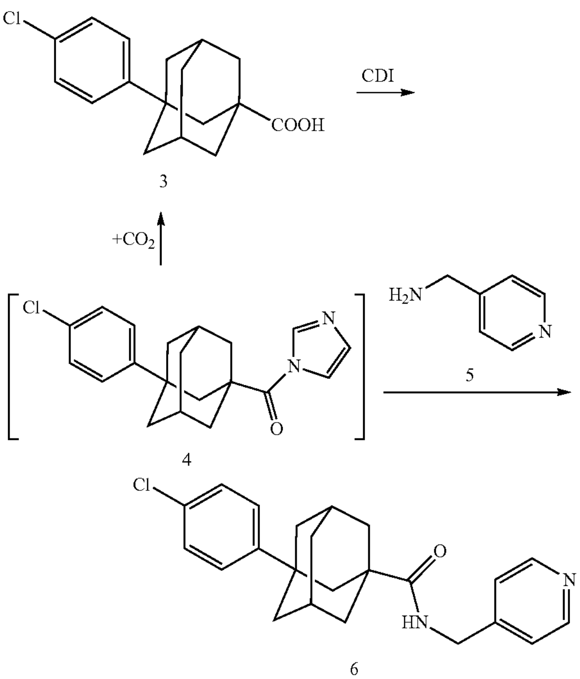

3

4

6

A diverse set of substituted aryladamantanes can be efficiently synthesized by condensation of various aromatic compounds with 2, and a variety of such compounds are commercially available. Additionally, amidation of 3 can be efficiently completed using a variety of coupling reagents and primary amine-containing compounds. The following Example provides several representatives of the products of this process; however, these methods can be adapted to produce many structurally related adamantylamides that are considered to be subjects of this invention. For a full disclosure of these methods, U.S. Pat. No. 7,338,961 is incorporated herein by reference for the teachings therein.

Example 3

ABC294640 Increases the Expression of Calreticulin on the Surface of Tumor Cells One indicator that tumor cells are undergoing immunogenic cell death (ICD) is increased expression of calreticulin on the surface of the cells. Calreticulin is normally expressed in the endoplasmic reticulum (ER) of cells; however, when cells are treated with an agent that promotes ER stress, calreticulin expression can be observed on the external surface of the cells. Promotion of ER stress is a typical mechanism for inducing ICD, and therefore measuring the surface expression of calreticulin is an established method for determining if a compound causes ICD. The effects of ABC294640, an inhibitor of sphingosine kinase-2, on the surface expression of calreticulin in several different types of tumor cells were examined. In these experiments, the test tumor cells were incubated with ABC294640 at varying concentrations, and the cells were harvested at 4-24 hours after the addition of ABC294640. The cells were then incubated with a fluorescently labeled antibody that selectively binds to calreticulin, washed and then analyzed by flow cytometry to quantify the amount of surface calreticulin on many individual cells. The resulting data is analyzed by determining the geometric mean of the fluorescence intensity for the population of cells using algorithms well known in the field of flow cytometry. Data provided in Table 1 summarizes the effects of treatment with ABC294640 on surface expression of calreticulin in a panel of tumor cells. For each cell type, samples treated with dimethylsulfoxide (DMSO, the solvent used to dissolve ABC294640) or 40 μM ABC294640 for a period of 24 hours. The geometric mean of the fluorescence intensity for cell samples treated with DMSO was expressed as 1.0 and the data for cell samples treated with ABC294640 were expressed relative to the DMSO control. In all cases, treatment with ABC294640 caused increased surface expression of calreticulin, with responses ranging from 1.46 to 3.64. It should be noted that this data is calculated on a logarithmic scale, so that a geometric mean fluorescence of 2.0 indicates a 10-fold increase in the amount of surface calreticulin. In summary, treatment with ABC294640 increased surface calreticulin expression between approximately 3-fold to >400-fold in pancreas, prostate, neuroblastoma, breast, lung and melanoma tumor cells. Therefore, ABC294640 increased ICD in a broad range of tumors.

TABLE 1

ABC294640 promotes the surface expression of calreticulin in a range of tumor cell lines.

| Tissue | Cell Line | Surface calreticulin expression (Geometric mean of fluorescence intensity) Control | 40 μM ABC294640 |
|---|---|---|---|
| Pancreas | PAN02 | 1.0 | 2.31 |
| Prostate | TRAMP-C2 | 1.0 | 3.64 |
| Neuroblastoma | Neuro-2a | 1.0 | 3.0 |
| Breast | E0771 | 1.0 | 1.46 |
| Lung | Lewis Lung carcinoma | 1.0 | 3.0 |
| Melanoma | B16-F10 | 1.0 | 2.7 |

Example 4

In Vivo Demonstration that ABC294640 Induces Immunogenic Cell Death in B16 Tumor Cells The ability of ABC294640 to induce ICD was evaluated using a syngeneic mouse model in which murine melanoma B16 cells (ATCC CRL-6322) were treated in vitro with ABC294640 and then were implanted subcutaneously into immune competent (C57BL/6) mice. C57Bl/6 mice (6-8 weeks old, male) were obtained from Jackson Labs and were maintained under standard conditions with food and water provided ad libitum. Clinical grade ABC294640 (BatchCHP110607) was manufactured under a GMP contract by ChemPacific Corporation (Baltimore, MD) and used for all studies. B16 cells were obtained from ATCC and cultured under standard conditions in Dulbecco's Modified Eagle's Medium with 10% fetal bovine serum. The B16 cells were treated in culture with a concentration of ABC294640 known to cause cell death for 24 hours to induce cell death—the cells were treated with 40 μM ABC294640. ABC296460-treated cells were then harvested by trypsinizing the cultures and scraping the cells of the plates, suspended in phosphate-buffered saline (PBS) and injected (500,000 dying cells) in the left hind flank subcutaneously in 0.1 ml total volume. The Control group was injected in the left hind flank with PBS alone. After 7 days, mice in both groups (n=10/group) were implanted with 100,000 untreated B16 cells on the right hind flank. Tumor growth was measured with digital calipers three times per week, and tumor volumes were calculated using the formula, $(L \times W^2)/2$. Mice were euthanized when tumor volumes reached ≥3,000 $mm^3$. FIG. 1 shows data for B16 tumor size on Day 14 after implantation into either PBS-pretreated mice (Control) or mice pretreated with ABC294640-treated B16 cells (immunized). Tumors in the control mice reached an average size of 2344±361 $mm^3$ on Day 14. In contrast, cells injected into the immunized mice reached an average size of only 641±210 $mm^3$ on Day 14 ($p=0.0007$). These data demonstrate that treatment of B16 tumor cells with ABC294640 causes ICD which markedly reduces tumor growth in subsequently challenged mice.

Example 5

Figure 2:
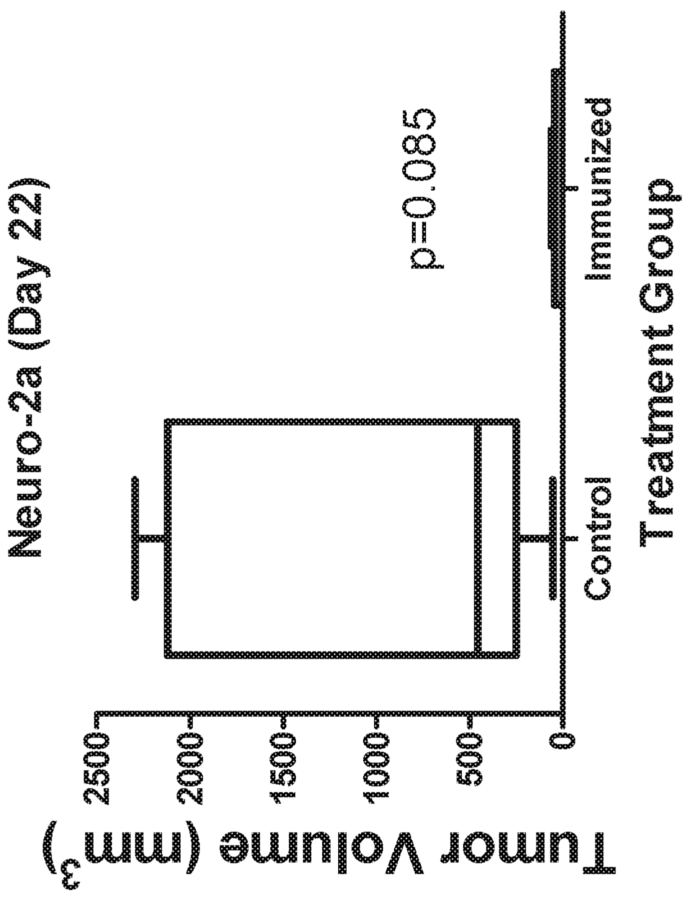
FIG. 2 shows that administration of ABC294640-treated Neuro-2a neuroblastoma cells elicits immunity against subsequently injected untreated Neuro-2a tumor cells. This is further demonstration that ABC294640 induces immunogenic cell death in tumor cells.

In Vivo Demonstration that ABC294640 Induces Immunogenic Cell Death in Neuro-2a Tumor Cells In a second version of the experiment, the ability of ABC294640 to induce ICD was evaluated using a syngeneic mouse model in which murine Neuro-2a neuroblastoma cells were treated in vitro with ABC294640 and then were implanted subcutaneously into immune competent (A/J) mice. The sources of mice, ABC294640 and tumor cells were the same as detailed in Example 4. The Neuro-2a cells were treated in culture with a concentration of ABC294640 known to cause cell death for 24 hours to induce cell death—the cells were treated with 40 μM ABC294640. ABC294640-treated cells were then harvested by trypsinizing the cultures and scraping the cells off the plate, suspended in phosphate-buffered saline (PBS) and injected (5,000,000 dying cells) in the left hind flank subcutaneously in 0.1 ml total volume. The Control group was injected in the left hind flank with PBS alone. After 7 days, mice in both groups (n=4-5/group) were implanted with 1,000,000 untreated Neuro-2a cells on the right hind flank. Tumor growth was measured and tumor volumes were calculated as described in Example 1. FIG. 2 shows data for Neuro-2a tumor size on Day 22 after implantation into either PBS-pretreated mice (Control) or mice pretreated with ABC294640-treated Neuro-2a cells (immunized). Tumors in the control mice reached an average size of 1039±450 $mm^3$ on Day 22. In striking contrast, cells injected into the immunized mice reached an average size of only 15±15 $mm^3$ on Day 22 ($p=0.085$). Whereas all of the mice in the Control group had tumors, 75% of the Immunized group were without measurable tumors on Day 22. These data demonstrate that treatment of Neuro-2a tumor cells with ABC294640 causes ICD which markedly reduces tumor growth in subsequently challenged mice.

Example 6

Figure 3A:
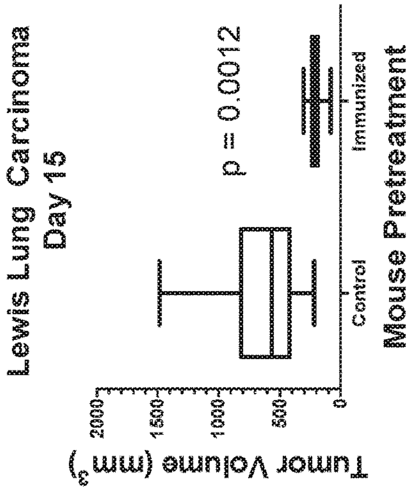
FIGS. 3A-3C shows that administration of ABC294640-treated Lewis Lung Carcinoma (LLC) cells elicits immunity against subsequently injected untreated LLC tumor cells. Tumor sizes are shown at day 15 (FIG. 3A), day 17 (FIG. 3B), and day 20 (FIG. 3C) to demonstrate that administration of the ABC294640-treated cells causes sustained suppression of tumor growth by untreated tumor cells. This is further demonstration that ABC294640 induces immunogenic cell death in tumor cells.
Figure 3B:
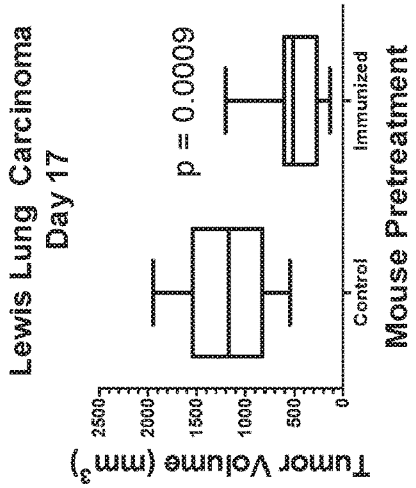
Figure 3C:
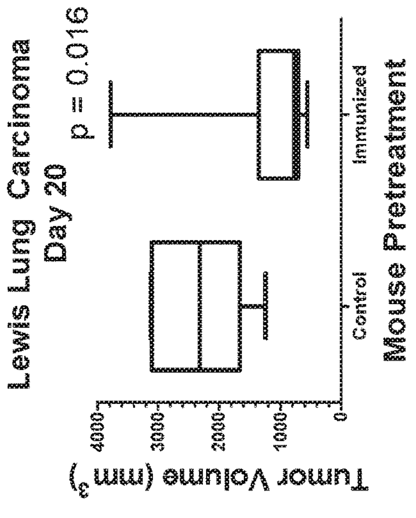

In Vivo Demonstration that ABC294640 Induces Immunogenic Cell Death in Lewis Lung Carcinoma (LLC) Tumor Cells In a third version of the experiment, the ability of ABC294640 to induce ICD was evaluated using a syngeneic mouse model in which murine LLC cells (ATCC CRL-1642) were treated in vitro with ABC294640 and then were implanted subcutaneously into immune competent (C57BL/6) mice. The sources of mice, ABC294640 and tumor cells were the same as detailed in Example 4. The LLC cells were treated in culture with 40 μM ABC294640 for 24 hours to induce cell death. ABC294640-treated cells were then harvested by trypsinizing the cultures and scraping the cells off the plates, suspended in phosphate-buffered saline (PBS) and injected (5,000,000 dying cells) in the left hind flank subcutaneously in 0.1 ml total volume. The Control group was injected in the left hind flank with PBS alone. After 7 days, mice in both groups (n=10/group) were implanted with 1,000,000 untreated LLC cells on the right hind flank. Tumor growth was measured and tumor volumes were calculated as described in Example 1. FIGS. 3A-3C shows data for LLC tumor size on Days 15, 17 and 20 after implantation into either PBS-pretreated mice (Control) or mice pretreated with ABC294640-treated LLC cells (immunized). Tumors in the control mice progressively increased over the course of the experiment, reaching average sizes of 651±114, 1190±143 and 2263±227 $smm^3$ on Days 15, 17 and 20, respectively. In contrast, cells injected into the immunized mice reached an average size of 209±18 (p=0.0012), 510±94 (p=0.0009) and 1220±320 (p=0.016) $mm^3$ on Day 15, 17 and 20, respectively. These data demonstrate that treatment of LLC tumor cells with ABC294640 causes ICD which markedly reduces tumor growth in subsequently challenged mice.

Example 7

In Vivo Demonstration that ABC294640 Induces Cross-Over Immunity

The Examples above demonstrate that in vitro treatment of multiple tumor cell lines with ABC294640 followed by administration of the treated cells to normal mice suppresses the growth of subsequently administered untreated samples of the same tumor cells. In the following study, the hypothesis that administration of one type of ABC294640-treated tumor cells suppresses growth of not only the same type of tumor cell, but also provide "cross-over" immunity to different types of tumor cells was tested. The sources of mice, ABC294640 and tumor cells were the same as detailed in previous Examples. Separately, B16 or LLC cells were treated in culture with 40 μM ABC294640 for 24 hours to induce cell death. ABC294640-treated B16 or LLC cells were then harvested by trypsinizing the cultures and scraping the cells off the plates, suspended in phosphate-buffered saline (PBS) and injected (500,000 dying B16 cells or 5,000,000 dying LLC cells) in the left hind flank subcutaneously in 0.1 ml total volume. The Control mice were injected in the left hind flank with PBS alone. After 7 days, mice were randomized into 4 groups as summarized below, were challenged with either 100,000 live B16 cells or 1,000,000 live LLC cells on the right hind flank to evaluate tumor growth. Thus, the "cross-over" test groups are: Group 3 comprised of mice immunized with ABC294640-treated lung carcinoma cells and challenged with untreated melanoma cells; and Group 6 comprised of mice immunized with ABC294640-treated melanoma cells and challenged with untreated lung carcinoma cells.

| Group | Number of Mice | First treatment | Second treatment |
|---|---|---|---|
| 1 | 6 | PBS | Untreated B16 cells |
| 2 | 7 | ABC294640-treated B16 cells | Untreated B16 cells |
| 3 | 7 | ABC294640-treated LLC cells | Untreated B16 cells |
| 4 | 6 | PBS | Untreated LLC cells |
| 5 | 7 | ABC294640-treated B16 cells | Untreated LLC cells |
| 6 | 7 | ABC294640-treated LLC cells | Untreated LLC cells |

Figure 4:
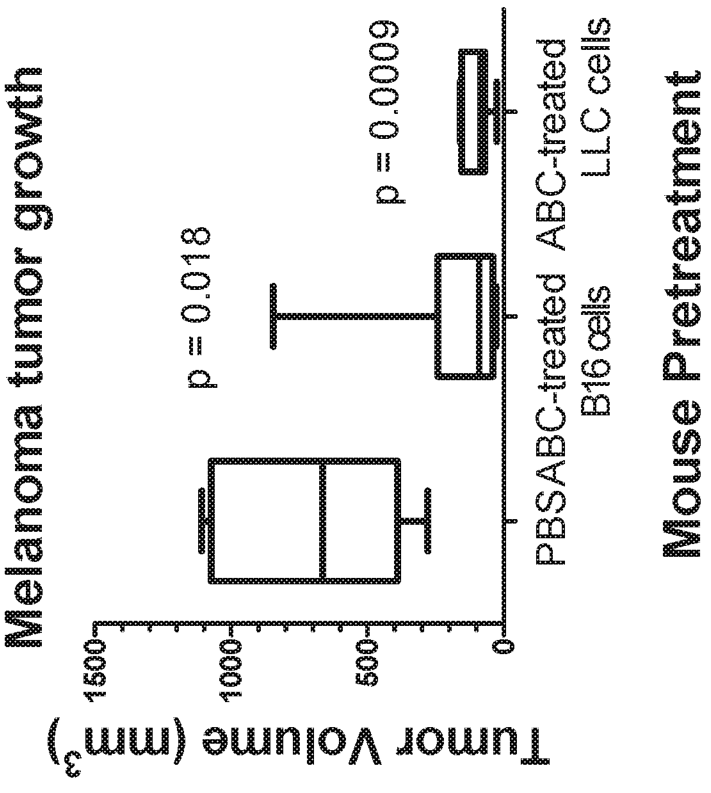
FIG. 4 shows that administration of ABC294640-treated B16 melanoma or Lewis Lung Carcinoma (LLC) cells elicits immunity against subsequently injected untreated B16 tumor cells. This is demonstration that ABC294640 induces cross-over immunity.
Figure 5:
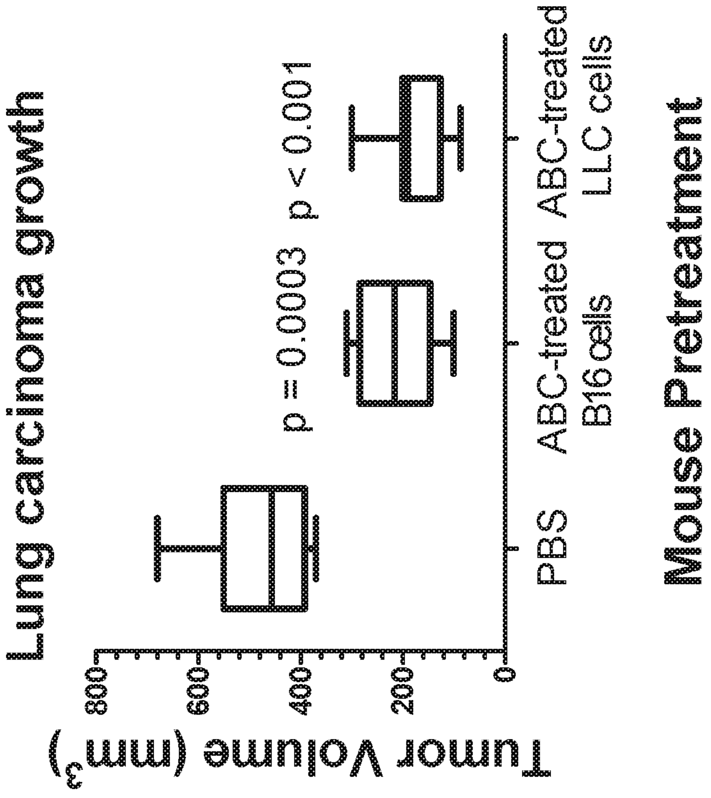
FIG. 5 shows that administration of ABC294640-treated B16 melanoma or Lewis Lung Carcinoma (LLC) cells elicits immunity against subsequently injected untreated LLC tumor cells. This is further demonstration that ABC294640 induces cross-over immunity.

Tumor growth was measured, and tumor volumes were calculated as described in Example 1. Mice were euthanized when tumor volumes reached ≥3,000 $mm^3$. FIG. 4 shows data for B16 tumor size on Day 19 after implantation into either PBS-pretreated mice (Control), mice pretreated with ABC294640-treated B16 cells or mice pretreated with ABC294640-treated LLC cells. Tumors in the control mice reached an average size of 702±144 $mm^3$. In contrast, cells injected into the B16 immunized mice reached an average size of 203±15 $mm^3$ (p=0.018); while cells injected into the LLC immunized mice reached an average size of 102±51 $mm^3$ (p=0.0009). Thus, vaccination with either ABC294640-treated melanoma or lung carcinoma cells suppressed the subsequent growth of untreated melanoma cells. FIG. 5 shows data for LLC tumor size on Day 28 after implantation into either PBS-pretreated mice (Control), mice pretreated with ABC294640-treated B16 cells or mice pretreated with ABC294640-treated LLC cells. Tumors in the control mice reached an average size of 479±113 $mm^3$. In contrast, cells injected into the B16 immunized mice reached an average size of 208±74 $mm^3$ (p=0.0003); while cells injected into the LLC immunized mice reached an average size of 177±68 $mm^3$ ($p<0.001$). Thus, vaccination with either ABC294640-treated melanoma or lung carcinoma cells suppressed the subsequent growth of untreated lung carcinoma cells. These data demonstrate that in vitro treatment of tumor cells with ABC294640 promotes immunity to multiple tumor types in subsequently challenged mice.

Example 8

In Vivo Antitumor Activity of ABC294640 in Combination with Anti-PD-1 Antibody

Figure 6:
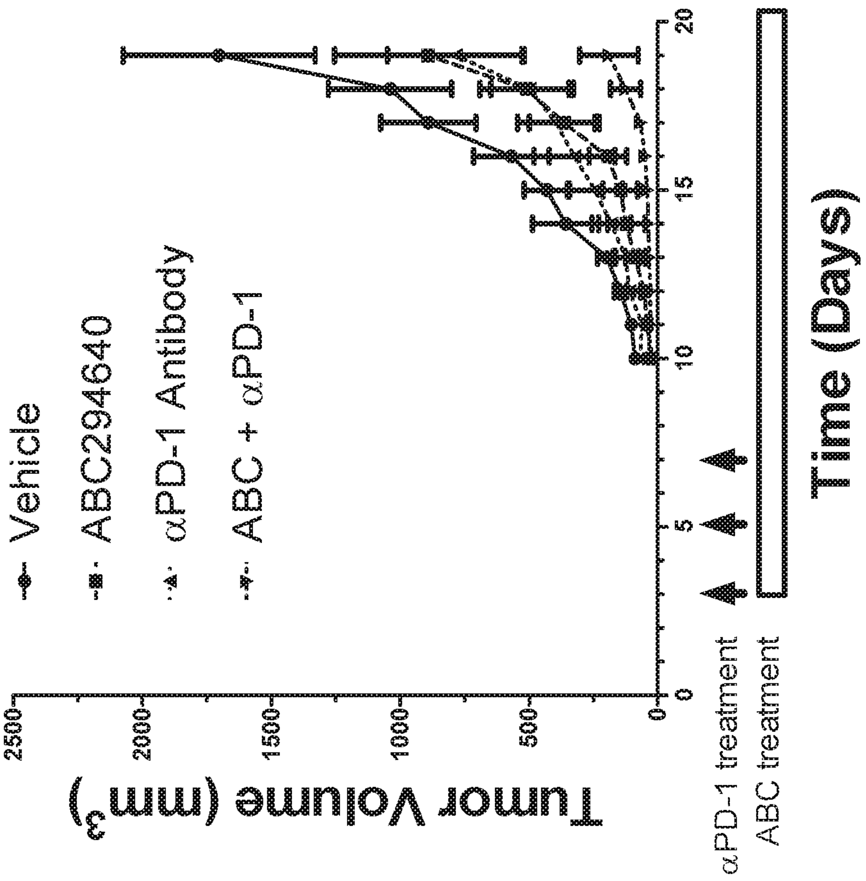
FIG. 6 shows that the growth of B16 melanoma tumors is partially inhibited by treatment of the mice with either ABC294640 (ABC) alone or anti-PD-1 antibody alone. Treatment of mice with a combination of ABC294640 plus anti-PD-1 antibody resulted in markedly increased suppression of tumor growth. Symbols indicate the average tumor volume and error bars indicate the standard error of the mean for each treatment group at the indicated times.
Figure 7:
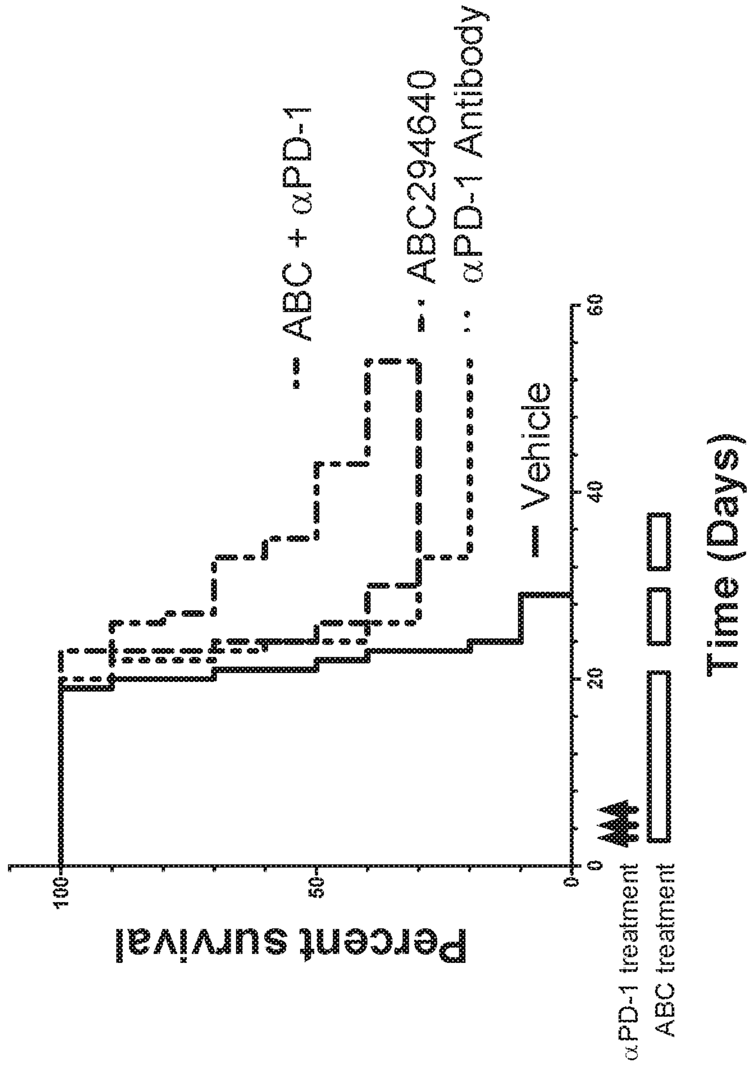
FIG. 7 shows that the survival of mice bearing B16 melanoma tumors is slightly prolonged by treatment of the mice with either ABC294640 (ABC) alone or anti-PD-1 antibody alone. Treatment of mice with a combination of ABC294640 plus anti-PD-1 antibody resulted in markedly increased survival of the tumor-bearing mice.

Agents that induce ICD may enhance the antitumor activity of checkpoint antibodies. Because the data described above clearly demonstrates that ABC294640 induces ICD in several types of cancer, the combined effects of treating tumor-bearing mice with ABC294640 and anti-PD-1 antibody were examined in the B16 tumor model. Anti-mouse PD-1 (Catalog number BE0146) antibody was purchased from BioXCell (West Lebanon, NH). C57BL/6 mice were injected with 100,000 B16 cells suspended in PBS into the right hind flank subcutaneously on Day 0 of the experiment. Mice were randomized on Day 3 of the experiment into the following four treatment groups (n=10/group): Control (vehicle only); ABC294640 alone; anti-PD-1 antibody alone; and ABC294640 in combination with anti-PD-1 antibody. ABC294640 was suspended in vehicle (46.7% PEG, 46.7% saline and 6.6% ethanol) and dosed by oral gavage at 50 mg/kg 5 days/week (i.e. days 3-7, 10-14, 17-21, etc.) until sacrifice. Anti-PD-1 antibody was suspended in sterile PBS, and administered by intraperitoneal (i.p.) injection at a dose of 200 μg/mouse on Days 3, 6 and 10. The combination treatment group mice received antibody and ABC294640 treatments concomitantly on days when antibody was scheduled. Control group mice received oral vehicle and/or sterile PBS i.p. on all days that treated mice received either ABC294640 or antibody. Tumors were measured with digital calipers three times per week and volumes were calculated using the formula, $(L\times W^2)/2$. Mice were euthanized when tumor volumes reached ≥3,000 $mm^3$. FIG. 6 demonstrates the growth of B16 tumors in this experiment. Tumors in the Control mice grew very aggressively after a lag of approximately 10 days. On Day 19, the average tumor volumes for the Control, ABC294640 alone, anti-PD-1 antibody alone, and combination treatment groups were 1702±373, 892±364, 783±265 and 190±114 $mm^3$, respectively. Tumor volumes for ABC294640 alone and anti-PD-1 antibody alone were not significantly different from the Control group; however, tumor volumes in the ABC294640 plus anti-PD-1 treatment group were highly significantly reduced compared with the Control group (p=0.0011). As directed by the IACUC protocol, each mouse was sacrificed when its tumor volume reached 3,000 $mm^3$. FIG. 7 shows survival curves for mice in this experiment. Mice in the Control group had a median survival of 21 days, and all animals were sacrificed by Day 29. Treatment with ABC294640 alone provided a median survival of 24 days and 30% of the mice were alive on Day 56 when the experiment was terminated (p=0.009). Similarly, treatment with anti-PD-1 alone enhanced median survival to 23 days (p=0.033), and resulted in 20% of the mice surviving to Day 56. The combination of ABC294640 plus anti-PD-1 antibody markedly increased median survival to 35 days, and 30% of these mice survived to Day 56 (p<0.0001). Therefore, combining ABC294640 with the PD-1 checkpoint antibody provides greatly improved antitumor activity and increases survival longer than does either agent alone.

Example 9

In Vivo Antitumor Activity of ABC294640 in Combination with Anti-CTLA4 Antibody

Figure 8:
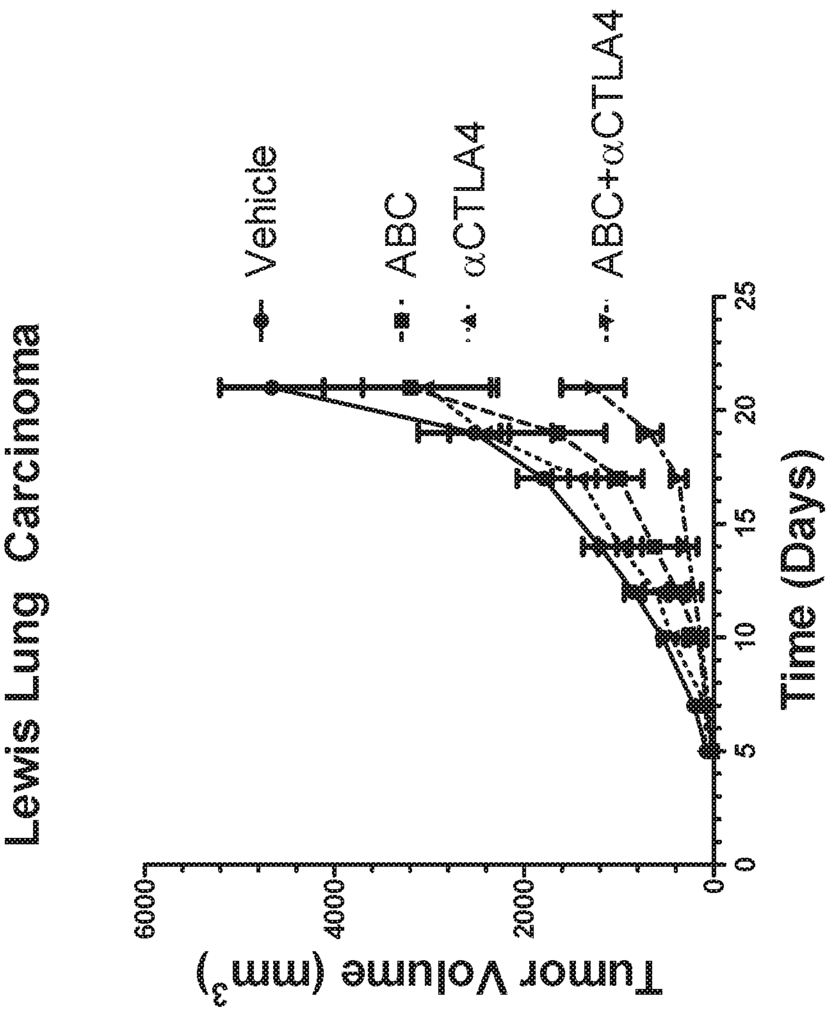
FIG. 8 shows that the growth of LLC lung tumors is partially inhibited by treatment of the mice with either ABC294640 (ABC) alone or anti-CTLA4 antibody alone. Treatment of mice with a combination of ABC294640 plus anti-CTLA4 antibody resulted in markedly increased suppression of tumor growth.
Figure 9:
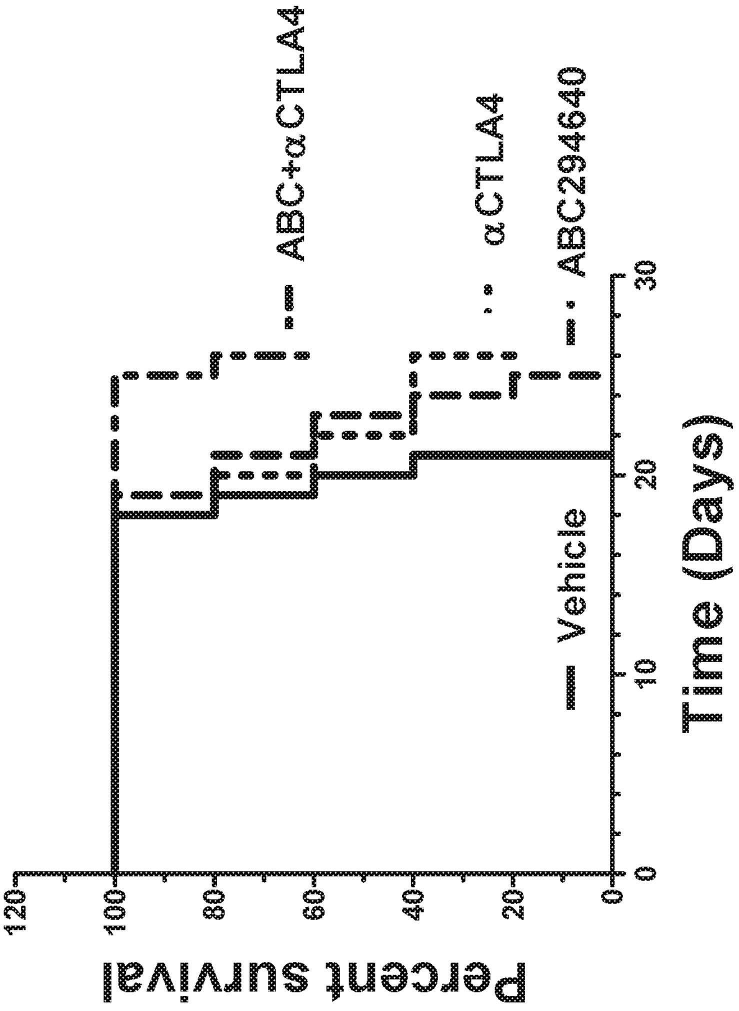
FIG. 9 shows that the survival of mice bearing LLC tumors is slightly prolonged by treatment of the mice with either ABC294640 (ABC) alone or anti-CTLA4 antibody alone. Treatment of mice with a combination of ABC294640 plus anti-CTLA4 antibody resulted in markedly increased survival of the tumor-bearing mice.

The combined effects of treating tumor-bearing mice with ABC294640 and anti-CTLA41 antibody were examined in the LLC tumor model. Anti-mouse CTLA-4 (catalog number BE0131) antibody was purchased from BioXCell (West Lebanon, NH). Mice were injected with 1,000,000 LLC cells suspended in PBS into the right hind flank subcutaneously on Day 0 of the experiment. Mice were randomized On Day 3 of the experiment into the following four treatment groups (n=5/group): Control (vehicle only); ABC294640 alone; anti-CTLA4 antibody alone; and ABC294640 in combination with anti-CTLA4 antibody. ABC294640 was suspended in vehicle (46.7% PEG, 46.7% saline and 6.6% ethanol) and dosed by oral gavage at 50 mg/kg 5 days/week (i.e. days 3-7, 10-14, 17-21, etc.) until sacrifice. Anti-CTLA4 antibody was suspended in dilution buffer (BioXCell, catalog number IP0070) and administered by intraperitoneal (i.p.) injection at a dose of 200 μg/mouse on Days 3, 6, 10, 13, 17 and 20. The combination treatment group mice received antibody and ABC294640 treatments concomitantly on days when antibody was scheduled. Control group mice received oral vehicle and/or sterile PBS i.p. on all days that treated mice received either ABC294640 or antibody. Tumors were measured with digital calipers three times per week and volumes were calculated using the formula, $(L \times W^2)/2$. Mice were euthanized when tumor volumes reached ≥3,000 $mm^3$. FIG. 8 demonstrates the growth of LLC tumors in this experiment. Tumors in the Control mice grew progressively after a lag of approximately 7 days. On Day 21, the average tumor volumes for the Control, ABC294640 alone, anti-CTLA4 antibody alone, and combination treatment groups were 4622±548, 3197±914, 3029±675 and 1274±336 $mm^3$, respectively. Tumor volumes for ABC294640 alone and anti-CTLA4 antibody alone were not significantly different from the Control group; however, tumor volumes in the ABC294640 plus anti-CTLA4 treatment group were highly significantly reduced compared with the Control group (p=0.0008). As directed by the IACUC protocol, each mouse was sacrificed when its tumor volume reached 3,000 $mm^3$. FIG. 9 shows survival curves for mice in this experiment. Mice in the Control group had a median survival of 19 days, and all animals were sacrificed by Day 21. Treatment with ABC294640 alone provided a median survival of 22 days; while treatment with anti-CTLA4 did not affect the median survival. The combination of ABC294640 plus anti-CTLA4 antibody increased median survival to >26 days, and 60% of these mice survived to Day 26. Therefore, combining ABC294640 with the CTLA4 checkpoint antibody provides significantly improved antitumor activity and increases survival longer than does either agent alone.

Example 10

In Vivo Antitumor Activity of ABC294640 in Combination with Anti-PD-L1 Antibody

The combined effects of treating tumor-bearing mice with ABC294640 and anti-PD-L1 antibody were examined in the B16 tumor model. Anti-mouse PD-L1 (catalog number BE0101) antibody was purchased from BioXCell (West Lebanon, NH). Mice were injected with 100,000 B16 cells suspended in PBS into the right hind flank subcutaneously on Day 0 of the experiment. When the tumor reached a volume of ≥300 $mm^3$, mice were randomized into the following four treatment groups (n=5-6/group): Control (vehicle only); ABC294640 alone; anti-PD-L1 antibody alone; and ABC294640 in combination with anti-PD-L1 antibody. The day of randomization is noted as Day 1 of the experiment for each mouse. ABC294640 was suspended in vehicle (46.7% PEG, 46.7% saline and 6.6% ethanol) and dosed by oral gavage at 50 mg/kg 5 days/week until sacrifice. Anti-PD-L1 antibody was suspended in dilution buffer (BioXCell, catalog number IP0070) and administered by intraperitoneal (i.p.) injection at a dose of 200 μg/mouse on Days 1, 3, 5 and 7. The combination treatment group mice received antibody and ABC294640 treatments concomitantly on days when antibody was scheduled. Control group mice received oral vehicle and/or sterile PBS i.p. on all days that treated mice received either ABC294640 or antibody. Tumors were measured with digital calipers three times per week and volumes were calculated using the formula, $(L \times W^2)/2$. Mice were euthanized when tumor volumes reached ≥3,000 $mm^3$. The following Table indicates the median survival for each treatment group.

| Group | Treatment | Number of Mice | Median Survival (Days) | Significance Compared with Control (p) |
|---|---|---|---|---|
| 1 | Vehicle | 6 | 8.5 | |
| 2 | ABC294640 alone | 5 | 10 | 0.19 |
| 3 | Anti-PD-L1 antibody alone | 6 | 10.5 | 0.2 |
| 4 | ABC294640 plus anti-PD-L1 antibody | 5 | 16 | 0.0029 |

Mice in the Control group had a median survival of 8.5 days, and all animals were sacrificed by Day 12. Treatment with ABC294640 alone or anti-PD-L1 alone provided median survivals of 10 and 10.5 days, respectively. The combination of ABC294640 plus anti-PD-L1 antibody increased median survival to 16 days (p=0.0029 compared with Control). Therefore, combining ABC294640 with the PD-L1 checkpoint antibody provides significantly improved antitumor activity and increases survival longer than does either agent alone.

Disclosed herein is a method of treating cancer in a subject comprising administering to the subject an effective amount of an inhibitor of sphingosine kinase (SK) and an effective amount of a checkpoint inhibitor. In an embodiment, the checkpoint inhibitor can be an antibody directed toward CTLA4 (for example Ipilimumab) or directed toward PD-1 (for example Pembrolizumab or Nivolumab) or directed toward PD-L1 (for example Atezolizumab or Durvalumab). Other antibodies or chemical inhibitors targeting these pathways are also within the scope of this invention. For example, additional inhibitors of the PD-L1 pathway include BMS-936559, MPDL3280A, BMS-936558, MK-3475, CT-011, or MEDI4736.

In an embodiment, tumor cells can be isolated from the blood or affected tissue of a cancer patient and treated ex vivo with ABC294640 for approximately 24 hours. The treated cells can then be delivered to the bloodstream of the patient to promote an immune response to the cancer.

In an embodiment, the inhibitor of sphingosine kinase is a compound represented by formula I:

(I)

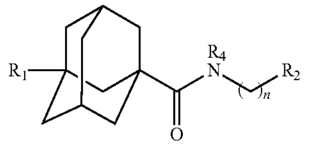

or a pharmaceutically acceptable salt thereof, wherein: Riis phenyl, 4-chlorophenyl or 4-fluorophenyl, $R_2$ is 4-pyridyl, optionally substituted with up to 4 groups that are independently $(C_1\text{-}C_6)$alkyl, halogen, haloalkyl, —OC(O) $(C_1\text{-}C_6$ alkyl), —C(O)O$(C_1\text{-}C_6$ alkyl), —CONR'R", —OC(O)NR'R", —NR'C(O)R", —$CF_3$, —$OCF_3$, —OH, $C_1\text{-}C_6$ alkoxy, hydroxyalkyl, —CN, —$CO_2H$, —SH, —S-alkyl, —SOR'R", —$SO_2R'$, —$NO_2$, or NR'R", wherein R' and R" are independently H or $(C_1\text{-}C_6)$alkyl, and wherein each alkyl portion of a substituent is optionally further substituted with 1, 2, or 3 groups independently selected from halogen, CN, OH, and $NH_2$, $R_4$ is H or alkyl, and n is 1 or 2. In an embodiment, the inhibitor of sphingosine kinase is:

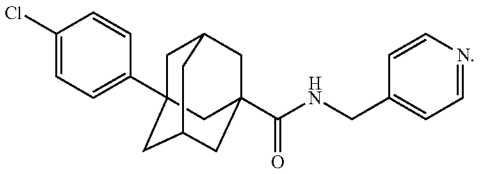

3-(4-Chloro-phenyl)-adamantane-1-carboxylic acid (pyridin-4-ylmethyl)-amide

In an embodiment, the treating cancer is further defined as reducing the size of a tumor or inhibiting growth of a tumor. In an embodiment, the inhibitors are administered to the subject at least two, three, four, five, six, seven, eight, nine or ten times. In an embodiment, the subject is further administered a second cancer therapy. In an embodiment, the second cancer therapy comprises surgery, radiotherapy, chemotherapy, toxin therapy, immunotherapy, cryotherapy or gene therapy. In an embodiment, the melanoma is a chemotherapy or radio-resistant melanoma. In an embodiment, the effective amount comprises at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 20, 30, 40, 50, 60, 70, 80, 90, 100, 150, 200, 250, or 300 μg/kg or mg/kg per subject weight.

A method of preparing immunologically primed cancer cells using cancer cells collected from a patient includes treating the cancer cells, ex vivo, with a toxic concentration of a compound that modifies sphingolipid metabolism, wherein the toxic concentration is sufficient to induce immunogenic cell death in the cancer cells. In an embodiment, the compound that modifies sphingolipid metabolism is an inhibitor of a sphingosine kinase. In an embodiment, the compound that is an inhibitor of a sphingosine kinase is a selective inhibitor of sphingosine kinase-2 (SK2). In an embodiment, the selective inhibitor of SK2 is 3-(4-Chlorophenyl)-adamantane-1-carboxylic acid (pyridin-4-ylmethyl)-amide compound or a pharmaceutically acceptable salt thereof. In an embodiment, the collected cancer cells are treated for at least 24 hours. In an embodiment, the toxic concentration of the selective inhibitor of SK2 is from about 20 μM to about 60 μM. In an embodiment, the immunologically primed cancer cells overexpress calreticulin on their surface. In an embodiment, the cancer cells are immune cells. In an embodiment, the immunologically primed cancer cells express calreticulin on their surface about 3-fold or more (e.g. from about 3-fold to about 400-fold or more) than non-primed cancer cells. In some embodiments, the immunologically primed cancer cells express calreticulin on their surface about 3-fold, about 4-fold, about 5-fold, about 6-fold, about 7-fold, about 8-fold, about 9-fold, about 10-fold, about 15-fold, about 20-fold, about 30-fold, about 40-fold, about 50-fold, about 60-fold, about 70-fold, about 80-fold, about 90-fold, about 100-fold, about 150-fold, about 200-fold, about 250-fold, about 300-fold, about 350-fold, about 400-fold or more than non-primed cancer cells. In some embodiments, the immunologically primed cancer cells express calreticulin on their surface from about 3-fold to about 10-fold, from about 3-fold to about 50-fold, from about 3-fold to about 100-fold, from about 3-fold to about 150-fold, from about 3-fold to about 200-fold, from about 3-fold to about 250-fold, from about 3-fold to about 300-fold, from about 3-fold to about 350-fold, from about 3-fold to about 400-fold or more than non-primed cancer cells. In some embodiments, the immunologically primed cancer cells express calreticulin on their surface from about 10-fold to about 50-fold, from about 10-fold to about 100-fold, from about 10-fold to about 150-fold, from about 10-fold to about 200-fold, from about 10-fold to about 250-fold, from about 10-fold to about 300-fold, from about 10-fold to about 350-fold, from about 10-fold to about 400-fold or more than non-primed cancer cells. In some embodiments, the immunologically primed cancer cells express calreticulin on their surface from about 50-fold to about 100-fold, from about 50-fold to about 150-fold, from about 50-fold to about 200-fold, from about 50-fold to about 250-fold, from about 50-fold to about 300-fold, from about 50-fold to about 350-fold, from about 50-fold to about 400-fold or more than non-primed cancer cells. In some embodiments, the immunologically primed cancer cells express calreticulin on their surface from about 100-fold to about 150-fold, from about 100-fold to about 200-fold, from about 100-fold to about 250-fold, from about 100-fold to about 300-fold, from about 100-fold to about 350-fold, from about 100-fold to about 400-fold or more than non-primed cancer cells. In some embodiments, the immunologically primed cancer cells express calreticulin on their surface from about 150-fold to about 200-fold, from about 150-fold to about 250-fold, from about 150-fold to about 300-fold, from about 150-fold to about 350-fold, from about 150-fold to about 400-fold or more than non-primed cancer cells. In some embodiments, the immunologically primed cancer cells express calreticulin on their surface from about 200-fold to about 250-fold, from about 200-fold to about 300-fold, from about 200-fold to about 350-fold, from about 200-fold to about 400-fold or more than non-primed cancer cells. In some embodiments, the immunologically primed cancer cells express calreticulin on their surface from about 250-fold to about 300-fold, from about 250-fold to about 350-fold, from about 250-fold to about 400-fold or more than non-primed cancer cells. In some embodiments, the immunologically primed cancer cells express calreticulin on their surface from about 300-fold to about 350-fold, from about 300-fold to about 400-fold or more than non-primed cancer cells. In some embodiments, the immunologically primed cancer cells express calreticulin on their surface from about 350-fold to about 400-fold or more than non-primed cancer cells. In an embodiment, the immune cells comprise T-cells, natural killer (NK) cells, or dendritic cells. In an embodiment, the cancer cells are hematologic cancer cells. In an embodiment, the hematologic cancer cells are leukemia cells. In an embodiment, the cancer cells are solid tumor cells. In an embodiment, the cancer cells are circulating tumor cells. In an embodiment, the method further comprises harvesting at least a portion of the immunologically primed cancer cells and suspending the cells in phosphate-buffered saline. In an embodiment, the method further comprises shipping at least a portion of the immunologically primed cancer cells to a point of the patient's care. In an embodiment, the point of the patient's care is a hospital. In an embodiment, the point of the patient's care is a cancer center. In an embodiment, the method further comprises administering at least a portion of the shipped immunologically primed cancer cells to the patient to elicit an immune response. In an embodiment, the immune response slows or stops the growth of cancer in the patient. In an embodiment, the immune response stops cancer from metastasizing in the patient. In an embodiment, the immune response makes the patient's immune system more efficient at killing cancer cells. In an embodiment, the method further comprises administering an effective amount of at least one checkpoint inhibitor.

An agent for treating cancer, comprising the immunologically primed cancer cells obtained by the methods according to the invention.

An immunologically primed cancer cell prepared by a method comprising the following steps: receiving cancer cells collected from a patient; and treating the collected cancer cells, ex vivo, with a toxic concentration of a compound that modifies sphingolipid metabolism to prepare the immunologically primed cancer cells, wherein the toxic concentration is sufficient to induce immunogenic cell death in the cancer cells. In an embodiment, the compound that modifies sphingolipid metabolism is an inhibitor of a sphingosine kinase. In an embodiment, the inhibitor of a sphingosine kinase is a selective inhibitor of sphingosine kinase-2 (SK2). In an embodiment, the selective inhibitor of SK2 is 3-(4-Chlorophenyl)-adamantane-1-carboxylic acid (pyridin-4-ylmethyl)-amide or a pharmaceutically acceptable salt thereof. In an embodiment, the collected cancer cells are treated for at least 24 hours. In an embodiment, the toxic concentration of the selective inhibitor of SK2 is from about 20 μM to about 60 μM. In an embodiment, the immunologically primed cancer cells overexpress calreticulin on their surface. In an embodiment, the immunologically primed cancer cells express calreticulin on their surface about 3-fold or more (e.g. from about 3-fold to about 400-fold or more) than non-primed cancer cells. In some embodiments, the immunologically primed cancer cells express calreticulin on their surface about 3-fold, about 4-fold, about 5-fold, about 6-fold, about 7-fold, about 8-fold, about 9-fold, about 10-fold, about 15-fold, about 20-fold, about 30-fold, about 40-fold, about 50-fold, about 60-fold, about 70-fold, about 80-fold, about 90-fold, about 100-fold, about 150-fold, about 200-fold, about 250-fold, about 300-fold, about 350-fold, about 400-fold or more than non-primed cancer cells. In some embodiments, the immunologically primed cancer cells express calreticulin on their surface from about 3-fold to about 10-fold, from about 3-fold to about 50-fold, from about 3-fold to about 100-fold, from about 3-fold to about 150-fold, from about 3-fold to about 200-fold, from about 3-fold to about 250-fold, from about 3-fold to about 300-fold, from about 3-fold to about 350-fold, from about 3-fold to about 400-fold or more than non-primed cancer cells. In some embodiments, the immunologically primed cancer cells express calreticulin on their surface from about 10-fold to about 50-fold, from about 10-fold to about 100-fold, from about 10-fold to about 150-fold, from about 10-fold to about 200-fold, from about 10-fold to about 250-fold, from about 10-fold to about 300-fold, from about 10-fold to about 350-fold, from about 10-fold to about 400-fold or more than non-primed cancer cells. In some embodiments, the immunologically primed cancer cells express calreticulin on their surface from about 50-fold to about 100-fold, from about 50-fold to about 150-fold, from about 50-fold to about 200-fold, from about 50-fold to about 250-fold, from about 50-fold to about 300-fold, from about 50-fold to about 350-fold, from about 50-fold to about 400-fold or more than non-primed cancer cells. In some embodiments, the immunologically primed cancer cells express calreticulin on their surface from about 100-fold to about 150-fold, from about 100-fold to about 200-fold, from about 100-fold to about 250-fold, from about 100-fold to about 300-fold, from about 100-fold to about 350-fold, from about 100-fold to about 400-fold or more than non-primed cancer cells. In some embodiments, the immunologically primed cancer cells express calreticulin on their surface from about 150-fold to about 200-fold, from about 150-fold to about 250-fold, from about 150-fold to about 300-fold, from about 150-fold to about 350-fold, from about 150-fold to about 400-fold or more than non-primed cancer cells. In some embodiments, the immunologically primed cancer cells express calreticulin on their surface from about 200-fold to about 250-fold, from about 200-fold to about 300-fold, from about 200-fold to about 350-fold, from about 200-fold to about 400-fold or more than non-primed cancer cells. In some embodiments, the immunologically primed cancer cells express calreticulin on their surface from about 250-fold to about 300-fold, from about 250-fold to about 350-fold, from about 250-fold to about 400-fold or more than non-primed cancer cells. In some embodiments, the immunologically primed cancer cells express calreticulin on their surface from about 300-fold to about 350-fold, from about 300-fold to about 400-fold or more than non-primed cancer cells. In some embodiments, the immunologically primed cancer cells express calreticulin on their surface from about 350-fold to about 400-fold or more than non-primed cancer cells. In an embodiment, the cancer cells are immune cells. In an embodiment, the immune cells comprise T-cells, natural killer (NK) cells, or dendritic cells. In an embodiment, the cancer cells are hematologic cancer cells. In an embodiment, the hematologic cancer cells are leukemia cells. In an embodiment, the cancer cells are solid tumor cells. In an embodiment, the cancer cells are circulating tumor cells. In an embodiment, a pharmaceutical composition comprises the immunologically primed cancer cells described above. In an embodiment, the pharmaceutical composition further comprises an effective amount of at least one checkpoint inhibitor. In an embodiment, there is disclosed use of the immunologically primed cancer cell described above in the preparation of a pharmaceutical composition for promoting an immune response in a patient. In an embodiment, the immune response slows or stops the growth of cancer in the patient. In an embodiment, the immune response stops cancer from metastasizing in the patient. In an embodiment, the immune response makes the patient's immune system more efficient at killing cancer cells.

Statement 1: An ex-vivo method to immunologically prime cancer cells collected from a patient, said method comprising a step of: treating cancer cells collected from a patient with a toxic concentration of a compound that modifies sphingolipid metabolism so as to induce immunogenic cell death in the collected cancer cells.

Statement 2: An ex-vivo method of producing immunologically primed cancer cells collected from a patient, said method comprising a step of: treating cancer cells collected from a patient with a toxic concentration of a compound that modifies sphingolipid metabolism so as to induce immunogenic cell death in the collected cancer cells thereby producing immunologically primed cancer cells.

Statement 3: Ex-vivo use of a compound that modifies sphingolipid metabolism to induce immunogenic cell death in cancer cells collected from a patient.

Statement 4a: The method of statement 1 or statement 2 or the use of statement 3, wherein the compound that modifies sphingolipid metabolism is an inhibitor of a sphingosine kinase.

Statement 4b: The method of statement 1 or statement 2 or the use of statement 3, wherein the toxic concentration of the compound that modifies sphingolipid metabolism is from about 20 μM to about 60 μM.

Statement 5: The method or use of statement 4a or 4b, wherein the inhibitor of a sphingosine kinase is a selective inhibitor of sphingosine kinase-2 (SK2).

Statement 6: The method or use of statement 5, wherein the selective inhibitor of SK2 is 3-(4-Chlorophenyl)-adamantane-1-carboxylic acid (pyridin-4-ylmethyl)-amide or a pharmaceutically acceptable salt thereof.

Statement 7: The method of any of statements 1, 2 or 4a to 6 or the use of any of statements 3 to 6, wherein the collected cancer cells are treated for at least 24 hours.

Statement 8: The method of any of statements 1, 2 or 4a to 7 or the use of any of statements 3 to 7, wherein the cancer cells are immune cells.

Statement 9: The method or use of statement 8, wherein the immune cells comprise T-cells, natural killer (NK) cells, or dendritic cells.

Statement 10: The method of any of statements 1, 2 or 4a to 7 or the use of any of statements 3 to 7, wherein the cancer cells are hematologic cancer cells.

Statement 11: The method or use of statement 10, wherein the hematologic cancer cells are leukemia cells.

Statement 12: The method any of statements 1, 2 or 4a to 7 or the use of any of statements 3 to 7, wherein the cancer cells are solid tumor cells.

Statement 13: The method of any of statements 1, 2 or 4a to 7 or the use of any of statements 3 to 7, wherein the cancer cells are circulating tumor cells.

Statement 14: The method of any of statements 1, 2 or 4a to 13 or the use of any of statements 3 to 13, further comprising: shipping at least a portion of the immunologically primed cancer cells to a point of the patient's care.

Statement 15: The method or use of statement 14, wherein the portion of shipped primed cancer cells includes dying cancer cells.

Statement 16: The method or use of statement 14 or 15, wherein the point of the patient's care is a hospital.

Statement 17: The method or use of statement 14 or 15, wherein the point of the patient's care is a cancer center.

Statement 18: Immunologically primed cancer cells produced by the method of any of statements 2 or 4 to 13 for use in medicine.

Statement 19: Immunologically primed cancer cells produced by the method of any of statements 2 or 4 to 13 for promoting an immune response to cancer cells in a patient.

Statement 20: Immunologically primed cancer cells produced by the method of any of statements 2 or 4 to 13 for use in slowing or stopping the growth of cancer in a patient.

Statement 21: Immunologically primed cancer cells produced by the method of any of statements 2 or 4 to 13 for use in stopping cancer from metastasizing in a patient.

Statement 22: Immunologically primed cancer cells produced by the method of any of statements 2 or 4 to 13 for use in making a patient's immune system more efficient at killing cancer cells.

Statement 23: Immunologically primed cancer cells produced by the method of any of statements 2 or 4 to 13 for use in a method of treating cancer.

Statement 24: Immunologically primed cancer cells for use according to statement 20, wherein said method further comprises administering an effective amount of at least one checkpoint inhibitor.

A method of treating cancer by enhancing or inducing an immunogenic cell death against cells in a subject in need thereof comprises administering to the subject an effective amount of a compound that modifies sphingolipid metabolism and administering to the subject an effective amount of an inhibitor of a checkpoint pathway. In an embodiment, the compound that modifies sphingolipid metabolism is an inhibitor of a sphingosine kinase. In an embodiment, the compound that is an inhibitor of a sphingosine kinase is a selective inhibitor of sphingosine kinase-2 (SK2). In an embodiment, the selective inhibitor of SK2 is 3-(4-Chlorophenyl)-adamantane-1-carboxylic acid (pyridin-4-ylmethyl)-amide compound or a pharmaceutically acceptable salt thereof. In an embodiment, the immunogenic cell death comprises an increased expression of calreticulin of the surface of the cancer cells. In an embodiment, the cancer cells are melanoma cells. In an embodiment, the cancer cells are lung cancer cells. In an embodiment, the inhibitor of the checkpoint pathway is an anti-PD-L1 antibody, an anti-PD-1 antibody or combinations thereof. In an embodiment, the checkpoint inhibitor pathway is an anti-CTLA4 antibody. In an embodiment, the anti-PD-L1 antibody or the ant-PD-1 antibody is a monoclonal antibody. In an embodiment, the anti-CTLA4 antibody is a monoclonal antibody. In an embodiment, the monoclonal antibody is a human antibody or a humanized antibody. In an embodiment, the administering is performed a plurality of times. In an embodiment, the subject is further administered a second cancer therapy. In an embodiment, the second cancer therapy comprises surgery, radiotherapy, chemotherapy, toxin therapy, immunotherapy, cryotherapy or gene therapy.

A kit comprises 3-(4-Chloro-phenyl)-adamantane-1-carboxylic acid (pyridin-4-ylmethyl)-amide compound or a pharmaceutically acceptable salt thereof; at least one checkpoint inhibitor; and instructions for use. In an embodiment, the at least one checkpoint inhibitor is a CTLA-4 receptor inhibitor, PD-1 receptor inhibitor, PD-L1 ligand inhibitor, PD-L2 ligand inhibitor, a LAG-3 receptor inhibitor, a TIM-3 receptor inhibitor, a BTLA receptor inhibitor, a KIR receptor inhibitor, or a combination of any of the foregoing checkpoint inhibitors. In an embodiment, the checkpoint inhibitor is an antibody or an antibody fragment. In an embodiment, the at least one checkpoint inhibitor is an anti-CTLA-4 receptor antibody, an anti-PD-1 receptor antibody, an anti-PD-L1 antibody, an anti-PD-L2 antibody, or a combination of any of the foregoing antibodies. In an embodiment, the at least one checkpoint inhibitor is in the form of a lyophilized solid. In an embodiment, the kit further comprises an aqueous reconstitution solvent. In an embodiment, the at least one checkpoint inhibitor is incorporated in a first pharmaceutically acceptable formulation and the 3-(4-Chloro-phenyl)-adamantane-1-carboxylic acid (pyridin-4-ylmethyl)-amide compound or a pharmaceutically acceptable salt thereof is incorporated in a second pharmaceutically acceptable formulation.

All publication, patents and patent applications cited herein are hereby incorporated by reference in their entirety for all purposes.

What is claimed is:

1. A method of treating lung cancer comprising administering to a subject in need thereof:

a therapeutically effective amount of a SK2 inhibitor which is 3-(4-Chlorophenyl)-adamantane-1-carboxylic acid (pyridin-4-ylmethyl)-amide or a pharmaceutically acceptable salt thereof; and a therapeutically effective amount of an anti-CTLA4 antibody.

2. The method of claim 1, wherein the anti-CTLA4 antibody is a monoclonal antibody.

3. The method of claim 2, wherein the monoclonal antibody is a human antibody or a humanized antibody.

4. The method of claim 1, wherein the therapeutically effective amount of the SK2 inhibitor and the therapeutically effective amount of the inhibitor of the anti-CTLA4 antibody are co-administered.

5. The method of claim 1, wherein the therapeutically effective amount of the SK2 inhibitor and the therapeutically effective amount of the inhibitor of the anti-CTLA4 antibody are administered separately.

* * * * *